United States Patent
Babcock et al.

(10) Patent No.: US 7,600,604 B2
(45) Date of Patent: Oct. 13, 2009

(54) USER DISPOSABLE MEMBER FOR USE WITHIN THE EAR CANAL AND METHODS FOR MANUFACTURING THE SAME

(75) Inventors: Martin P. Babcock, White Bear Lake, MN (US); Robert J. Oliveira, Maplewood, MN (US); William Parish, Maplewood, MN (US); Vasant V. Kolpe, Mendota Heights, MN (US); Michael T. Venem, St. Paul, MN (US)

(73) Assignee: Hearing Components, Inc., Oakdale, MN (US)

( * ) Notice: Subject to any disclaimer, the term of this patent is extended or adjusted under 35 U.S.C. 154(b) by 435 days.

(21) Appl. No.: 11/347,600

(22) Filed: Feb. 3, 2006

(65) Prior Publication Data

US 2006/0175722 A1  Aug. 10, 2006

Related U.S. Application Data

(60) Provisional application No. 60/650,202, filed on Feb. 4, 2005.

(51) Int. Cl.
*H04R 25/02* (2006.01)
*A61B 7/02* (2006.01)
*A61F 11/00* (2006.01)

(52) U.S. Cl. .................. 181/130; 181/135; 128/864
(58) Field of Classification Search ............... 181/130, 181/135; 128/864
See application file for complete search history.

(56) References Cited

U.S. PATENT DOCUMENTS

| | | | |
|---|---|---|---|
| 4,109,034 A | 8/1978 | Welch | |
| 4,216,177 A | 8/1980 | Otto | |
| 4,239,821 A | 12/1980 | McLean et al. | |
| 4,490,857 A * | 1/1985 | Leight et al. | 2/209 |
| 4,552,137 A * | 11/1985 | Strauss | 128/864 |
| 4,724,922 A * | 2/1988 | Kalayjian | 181/135 |
| 4,774,938 A * | 10/1988 | Leight | 128/864 |
| 4,880,076 A | 11/1989 | Ahlberg et al. | |
| 4,920,985 A | 5/1990 | Tindberg | |
| 4,969,534 A * | 11/1990 | Kolpe et al. | 181/130 |
| 5,002,151 A | 3/1991 | Oliveira et al. | |
| 5,044,463 A * | 9/1991 | Carr | 181/135 |
| 5,203,352 A * | 4/1993 | Gardner, Jr. | 128/864 |
| 5,229,138 A | 7/1993 | Carotti | |
| 5,333,622 A * | 8/1994 | Casali et al. | 128/864 |
| 5,350,544 A | 9/1994 | Bambara et al. | |
| 5,573,015 A * | 11/1996 | Williams | 128/864 |

(Continued)

FOREIGN PATENT DOCUMENTS

DE    1 905 618    12/1964

(Continued)

*Primary Examiner*—Jeffrey Donels
*Assistant Examiner*—Christina Russell
(74) *Attorney, Agent, or Firm*—Crompton, Seager & Tufte, LLC.

(57) ABSTRACT

A user-disposable member for placement and retention within the auditory anatomy, such as an ear canal. The user-disposable member includes a polymeric foam material, wherein the user-disposable member has a first portion having a peripheral outer surface having a first coefficient of friction, and a second portion having a peripheral outer surface having a second coefficient of friction different from the first coefficient of friction.

24 Claims, 17 Drawing Sheets

U.S. PATENT DOCUMENTS

| | | |
|---|---|---|
| 5,904,143 A | 5/1999 | Magidson et al. |
| 5,920,636 A | 7/1999 | Oliveira et al. |
| 6,086,802 A | 7/2000 | Levera et al. |
| 6,129,175 A * | 10/2000 | Tutor et al. .................. 181/135 |
| 6,310,961 B1 | 10/2001 | Oliveira et al. |
| 6,408,981 B1 * | 6/2002 | Smith et al. .................. 181/126 |
| 7,130,437 B2 * | 10/2006 | Stonikas et al. .............. 381/322 |
| 2005/0147269 A1 | 7/2005 | Oliveira et al. |

FOREIGN PATENT DOCUMENTS

| | | |
|---|---|---|
| DE | 39 29 060 A1 | 3/1991 |
| EP | 0 108 728 A2 | 5/1984 |

\* cited by examiner

USER DISPOSABLE MEMBER FOR USE WITHIN THE EAR CANAL AND METHODS FOR MANUFACTURING THE SAME

CROSS REFERENCE

This application claims priority to U.S. Provisional Application No. 60/650,202 filed on Feb. 4, 2005.

STATEMENT REGARDING FEDERALLY SPONSORED RESEARCH OR DEVELOPMENT

The subject matter of this application was funded in part with U.S. Government support under Grant No. 5R44DC7014-13 awarded by the National Institute of Health (NIH). The U.S. Government may have certain rights in this invention.

TECHNICAL FIELD

The present invention generally relates to sound control devices, and more specifically to user-disposable members for placement within the ear canal with improved insertion and/or retention which can be used to attenuate and/or transmit sound.

BACKGROUND

User-disposable polymeric foam members for placement within the auditory anatomy, such as the ear canal, of a user are useful to hold in place sound control devices, such as sound transmission and/or attenuation devices, or to attenuate unwanted sounds. It is desirable to provide an improved user-disposable member that has advantageous characteristics, and which may be readily manufactured in significant quantities.

SUMMARY

The disclosure is directed to a user-disposable polymeric foam member for use within the auditory anatomy, such as the ear canal or external ear, and methods of manufacturing the same.

Accordingly, one embodiment provides a user-disposable member for placement within an ear canal of a user. The user-disposable member includes a first portion having a peripheral outer surface and a second portion having a peripheral outer surface. The peripheral outer surface of the first portion may have a coefficient of friction dissimilar and higher than the coefficient of friction of the second portion.

Another embodiment provides a user-disposable member for placement within an ear canal including a generally cylindrical polymeric foam body. The foam body may include a first portion having a cut peripheral outer surface and a second portion having a molded peripheral outer surface. The molded outer surface provides dissimilar structural and surface properties from those of the cut outer surface.

An exemplary user-disposable member may be formed from polymeric foam material. For instance, a polymeric material may be continuously poured into a mold having one or more cavities formed therein. In some embodiments, the polymeric material may be poured to a sheet or layer thickness greater than the depth of the one or more cavities, and then cured to form a polymeric foam material of a predetermined generally uniform thickness excluding the depth of the cavities. The foam sheet, as formed, includes an elongate layer of foam having one or more projections extending from one side. The projections may substantially correspond to the cavities of the mold. A user-disposable member may be separated from the foam sheet by cutting a plug of foam material generally aligned with a projection from the polymeric foam layer, thus forming a user-disposable member having a first portion including a cut outer surface and a second portion having a molded outer surface.

Another embodiment includes a multilayered user-disposable member including at least two layers of dissimilar materials. A first portion of the user-disposable member may include a first layer of polymeric foam material, and a second portion of the user-disposable member may include a second layer of polymeric material dissimilar from the first layer of material. The first portion may include a peripheral outer surface with at least a portion having a first coefficient of friction, and the second portion may include a peripheral outer surface with at least a portion having a second coefficient of friction different from the first coefficient of friction. The coefficients of friction of the different portions may be due to the difference in material or as with other embodiments disclosed herein, the surface having a second coefficient of friction may be due to a lubricious layer, film skin or other means.

BRIEF DESCRIPTION OF THE DRAWINGS

The invention may be more completely understood in consideration of the following detailed description of various embodiments of the invention in connection with the accompanying drawings, in which.

Figure 1:
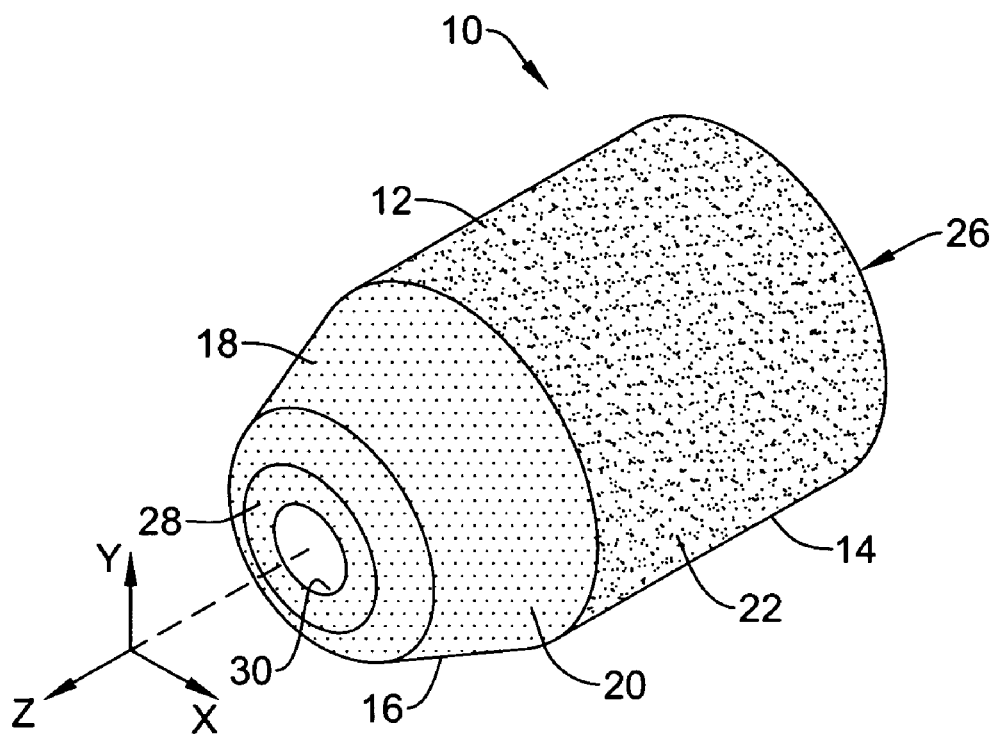
FIG. 1 is a perspective view of an exemplary user-disposable member.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification. As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The term "distal" as used herein is intended to describe that portion of an object positioned toward to the ear drum of a user, and the term "proximal" as used herein is intended to describe that portion of an object positioned away from the ear drum of a user.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to the figures, FIG. 1 illustrates an exemplary embodiment of a user-disposable member 10 (hereinafter member). The member 10 may be adapted to hold a sound control device, such as a sound transmission and/or attenuation device, at a proper position and with sufficient retention within a user's auditory anatomy, such as the ear canal or the external ear. Some embodiments of the member 10 may be useful with various types of sound controlling (e.g. transmitting or attenuating) devices, including, but not limited to, sound controlling devices that house speakers, microphones, and/or sound tubes adjacent their distal ends such as are used in some audio testing equipment, sound amplification devices, sound filtering devices, sound attenuation devices, audio devices, and sound controlling structures. The member 10 may be useful with devices that allow or facilitate communication in noisy environments. For example, the member 10 may allow some sounds or audio signals to travel through the ear canal while attenuating and/or filtering out undesired sounds or audio signals. For example, U.S. Pat. Nos. 4,880,076; 5,002,151; 5,920,636; and 6,310,961, the disclosures of which are incorporated herein by reference, show some exemplary user-disposable members. Additional exemplary user disposable members are disclosed in co-pending U.S. application Ser. No. 10/753,591, filed Jan. 7, 2004 and entitled EARBUD ADAPTER, the disclosure of which is incorporated herein by reference. In other embodiments, the member 10 may also be used independent of an additional device to attenuate sound. For example, the member 10 may be an earplug for insertion in the ear canal used to attenuate sound.

The member 10 may be formed of a polymeric material, such as a polymeric foam material. In some embodiments, the polymeric foam may have an open cell structure, a closed cell structure or a combination of open and closed cells, or, in other embodiments, the member 10 may include a first portion having a more open cell structure and a second portion having a more closed cell structure. In some embodiments, the member 10 may be formed of a resiliently compressible polymeric foam, such as a slow recovery foam. It may be desirable that the resiliently compressible polymeric foam be easily compressible so that it may be compressed and inserted into the ear canal where it may undergo recovery to a substantial portion of its original size. As the member 10 undergoes recovery, it may contact and closely conform to the surface of the ear canal, therefore, providing a secure and engaging fit within the ear canal. One such foam material is a viscoelastic polyurethane foam commercially available from 3M Company, St. Paul, Minn., similar to the foam sold by 3M under the trademark ATTENUTECH. Another suitable foam is a plasticized polyvinyl chloride foam commercially available from Aearo, Indianapolis, Ind. Although some suitable materials have been identified, one of skill in the art would understand that other suitable polymers may be used to provide desired properties to the member 10.

In some embodiments, the member 10 may include a generally cylindrical body portion, for example, as shown in FIG. 1. However, in other embodiments, the member 10 may include other shapes, such as fluted, bulbous, conical, frusta-conical, tapered, convex, concave, or other shaped portions. As shown in the illustrative embodiment, the body 12 may include a first portion 14 having a cylindrical shape and a second portion 16 having a frusta-conical shape. The body 12 may also include first and second portions 14, 16 each having a cylindrical shape, or the body 12 may include first and/or second portions 14, 16 having other desired shapes, such as radially fluted shapes, conical, frusta-conical, tapered, convex, or concave, for example. The member 10 could also have a generally oval cross section that more closely matches the ear canal cross section, with the member keyed to be properly rotated for insertion.

The first portion 14 has a peripheral outer surface 22 extending around the body 12 and located at a distance radially outward from the longitudinal axis of the body 12 of the member 10. The outer surface 22 has a first coefficient of friction. The second portion 16 has a peripheral outer surface 20 extending around the body and located at a distance radially outward from the longitudinal axis of the body 12 of the member 10. The outer surface 20 has a second coefficient of friction. The coefficient of friction of the outer surface 20 of the second portion 16 may be chosen to be different from the coefficient of friction of the outer surface 22 of the first portion 14. For example, the coefficient of friction of the outer surface 20 of the second portion 16 may be less than the coefficient of friction of the outer surface 22 of the first portion 14.

Figure 2:
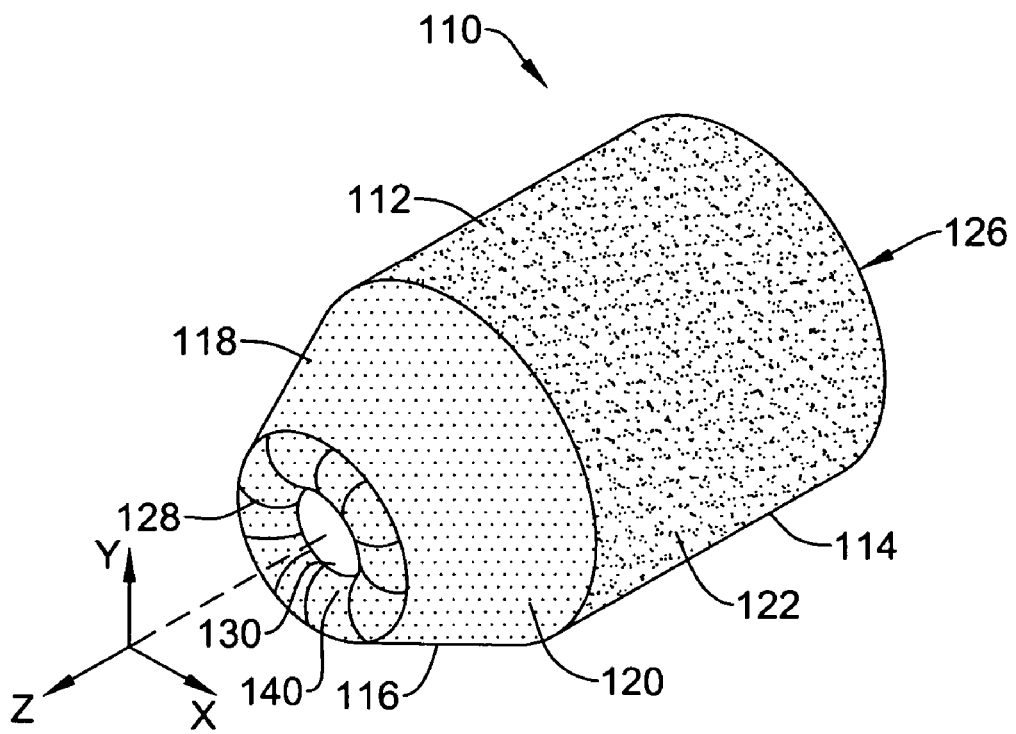
FIG. 2 is a perspective view of another exemplary user-disposable member.

A coordinate system has been included in FIGS. 1 and 2 for explanatory purposes. The longitudinal axis of the body 12 is intended to mean the central axis of the body 12 along the Z axis. Thus, a peripheral outer surface as described herein includes outer surfaces of the body 12 having, at least in part, a dimension in the longitudinally axial direction (i.e., having a dimension in the Z direction). Therefore, a cross-section taken perpendicular to the longitudinal axis will result in a cross-sectional area having a peripheral outer surface extending around the periphery of the cross-section. Thus, end surfaces having no or an inconsequential dimension in the Z direction are excluded from the definition of a peripheral outer surface as used herein. The coordinate system in FIGS. 1 and 2 may be adopted throughout the drawings of additional illustrative embodiments of a user-disposable member.

In some embodiments, the second portion 16 may be molded in a tapered profile, as shown in FIG. 1 and discussed in further detail later herein. The second portion 16 may have a skin layer 18 defining an outer surface 20 of the second portion 16. The skin layer 18 may be integrally formed as a result of a molding process, such as a molding process discussed herein, or the skin layer 18 may be formed in a subsequent process using chemical, thermal or mechanical treatments of the second portion 16. In other embodiments, the skin layer 18 may also be provided as an additional layer applied to the second portion 16 subsequent a molding process.

Figure 14:
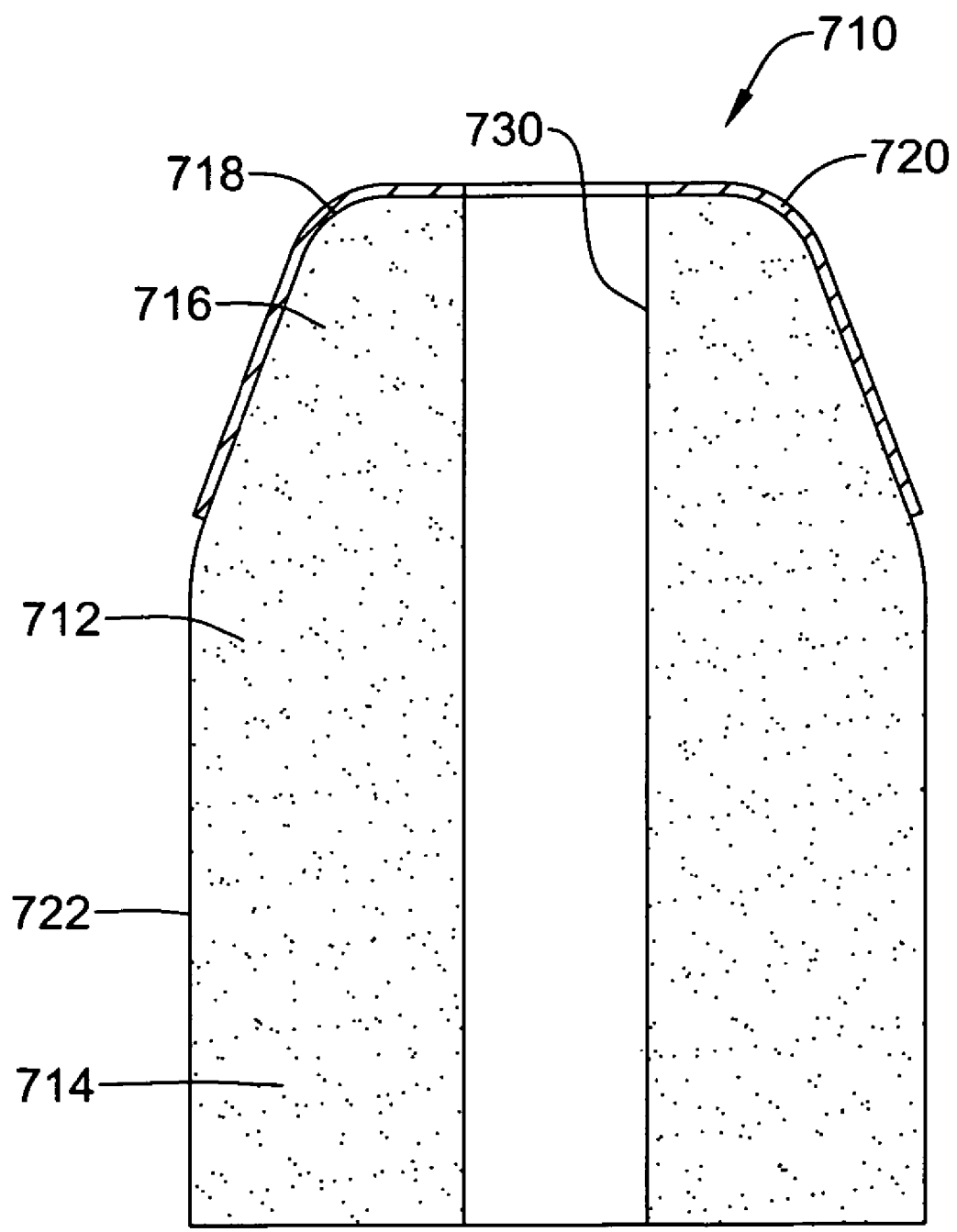
FIG. 14 is a cross-sectional view of another illustrative embodiment of a user-disposable member.

For instance, an alternative embodiment of a user-disposable member 710, shown in FIG. 14, includes an outer layer of material or film 718 provided on at least a portion of the second portion 716. The layer or film of material 718 may be a lubricious polymeric material, such as high or low density polyethylene, or other polymeric film. One possible material may be a micro-porous, or a non-porous, polyethylene film providing lubricity to the second portion 716. One exemplary low coefficient film would include a substantive lubricant film which stays on the foam during insertion (does not contaminate the ear canal or affect its surface) such as Emralon 8301. Other films could include Cotran 9720 or Code 749. Thus, the layer of material 718 may provide the peripheral outer surface 720 of at least the portion of the second portion 716 of the member 710 including the layer of material 718 with a lower coefficient of friction than the coefficient of friction of the outer surface 722 of the first portion 714 of the member 710. As illustrated in FIG. 14, the member 710 may include a lumen 730 extending into or through the body 712. However, in other embodiments, the body 712 may not include a lumen.

Again referring to FIG. 1, the first portion 14 may include a generally cylindrical portion having a peripheral outer surface 22. The outer surface 22 may be a cut peripheral outer surface, wherein the body 12 is cut from a larger piece of polymeric foam material. The cut peripheral outer surface 22 may have properties dissimilar to those of the molded peripheral outer surface 20. For instance, the cut outer surface 22 may be free of a skin layer, such as skin layer 18. The skin layer 18 may have a density greater that the density of the foam material. For example, the cut outer surface 22 may have a texture having a first coefficient of friction. The coefficient of friction of the cut outer surface 22 may provide the member 10 with sufficient or improved resistance to being pulled out of the ear canal and thus retains the member 10 within an ear canal. The molded outer surface 20 may have a texture having a second coefficient of friction different from the first coefficient of friction. For example, the coefficient of friction of the molded peripheral outer surface 20 may be less than the coefficient of friction of the cut peripheral outer surface 22. The molded outer surface 20 may provide the member 10 with sufficient smoothness and/or lubricity to easily insert the member 10 in an ear canal.

Alternatively or additionally, the cut outer surface 22 may have a first porosity, wherein the porosity is indicated by the ratio of the volume of interstices on the surface to the volume of mass on the surface. The molded outer surface 20 may have a second porosity different from the porosity of the cut outer surface 22. For example, the porosity of the molded outer surface 20 may be less than the porosity of the cut outer surface 22. In other words, the ratio of the volume of interstices on the surface to the volume of mass on the surface of the molded outer surface 20 may be less than the ratio on the cut outer surface 22. Viewed with the naked eye, the cut outer surface 22 may appear more porous than the molded outer surface 20, because the first portion 14 may have more visible cellular interstices than the second portion 16. The second portion 16 may have a substantially enclosed cellular structure on the outer surface 20. The enclosed cellular structure of the outer surface 20 may be the result of a molding process. In other words, the cut outer surface 22 may include cut cellular membranes visible subsequent a cutting process and the molded outer surface 20 may generally not include visible cut cellular membranes.

In other embodiments, the porosity of the peripheral outer surface 20 of the second portion 16 may be greater than the porosity of the peripheral outer surface 22 of the first portion 14. In other words, the ratio of the volume of interstices on the surface to the volume of mass on the surface of the peripheral outer surface 20 of the second portion 16 may be greater than the ratio on the peripheral outer surface 22 of the first portion 14. Therefore, viewed from the naked eye, the peripheral outer surface 22 of the first portion 14 may appear to be less porous than the peripheral outer surface 20 of the second portion 16, since the first portion 14 may have fewer visible cellular interstices than the second portion 16. Material can be selected to give desired coefficients of friction during insertion or controlled as discussed with other embodiments herein, such as film layer or skin.

Figure 3:
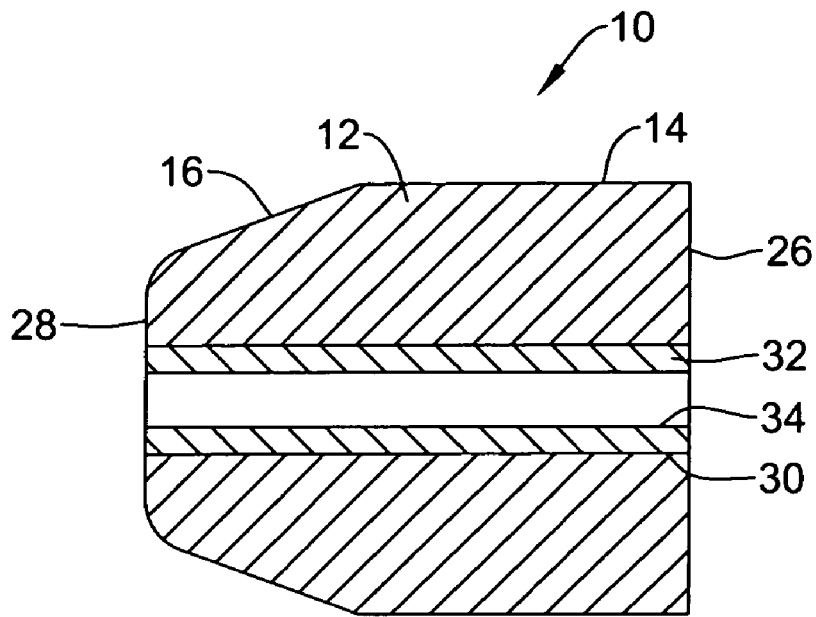
FIG. 3 is a cross-sectional view of the exemplary user-disposable member of FIG. 1.

The member 10 may include a lumen 30 extending through at least a portion of the member 10. In some embodiments, such as illustrated in FIG. 1, the member 10 may include a lumen 30 extending from a first end 26 to a second end 28 of the body 12. The lumen 30 may be configured to receive an elongate tubular member 32, as shown in FIG. 3. FIG. 3 is a cross-sectional view of the member 10 of FIG. 1, wherein the lumen 30 and the elongate tubular member 32 may more readily be understood. The elongate tubular member 32 may comprise a polymer, or other suitable material, giving the member 10 sufficient rigidity and/or retention properties. The elongate tubular member 32 may be secured to the member 10. For example, in some embodiments the elongate tubular member 32 may be adhesively bonded to the member 10. In other embodiments the elongate tubular member 32 may be thermally bonded to the member 10. In yet other embodiments, the elongate tubular member 32 may be positioned and affixed to the body 12 of the member 10 during the molding process forming the polymeric foam material of the body 12. The elongate tubular member 32 may include a lumen 34 extending therethrough. The lumen 34 may be sized and/or configured to receive a connecting portion of a sound control device. It is noted that in some applications, such as when the member 10 is used as an earplug, the lumen 30 and/or the elongate tubular member 32 may be absent from the member 10.

Figure 15A:
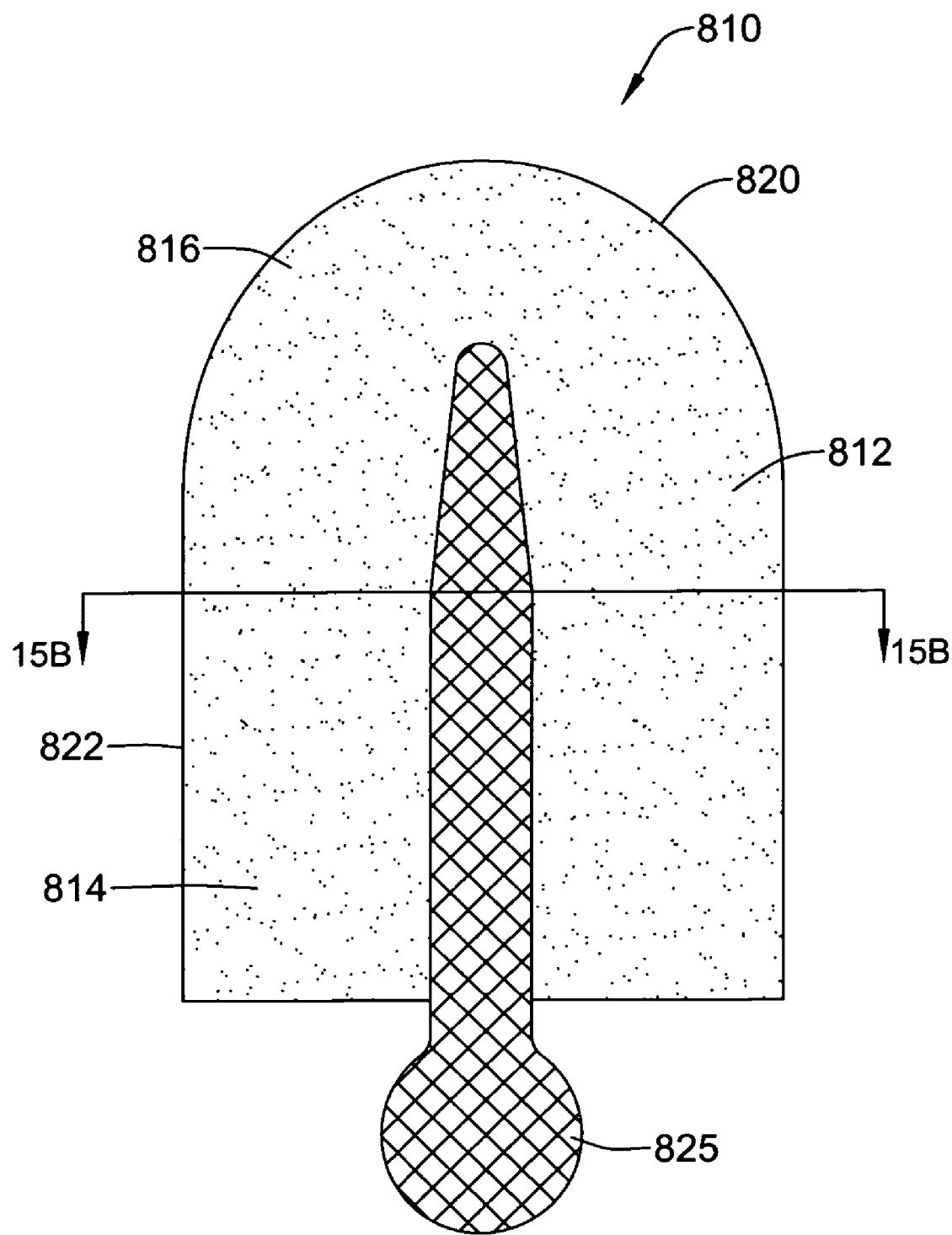
FIG. 15A is a cross-sectional view of another illustrative embodiment of a user-disposable member.

As a further example embodiment, the member 10 can include a central core, absent a lumen. For example, the illustrative embodiment of a user-disposable member 810, shown in FIG. 15A, includes a core member 825 disposed in a central portion of the body 812 of the member 810. The core member 825 may comprise a polymeric material giving the member 810 sufficient rigidity in some applications. For example, a user may grasp the portion of the core member 825 extending from the body 812 in order to position the member 810 in the user's ear canal. The core member 825 may extend into the second portion 816 and/or the first portion 814 of the body 812 a predetermined depth. The core member 825 may be affixed to the body 812 by any suitable means in order to assure against undesired separation of the core member 825 from the body 812. In some embodiments, the core member 825 may be positioned and affixed to the body 812 of the member 810 during the molding process forming the polymeric foam material of the body 812. Consequent the inclusion of the core member 825, the user need not directly contact the body 812 of the member 810. This may be advantageous in dirty environments where hygienic concerns disfavor direct contact with portions of the member 810 positioned in the ear canal of a user. The rigidity of the core member 825 facilitates insertion of the member 810 into the ear canal. As described with other embodiments, the peripheral outer surface 820 of the second portion 816, or more distal portion, may additionally have a coefficient of friction less than the coefficient of friction of the peripheral outer surface 822 of the first portion 814, or more proximal portion.

Figure 15B:
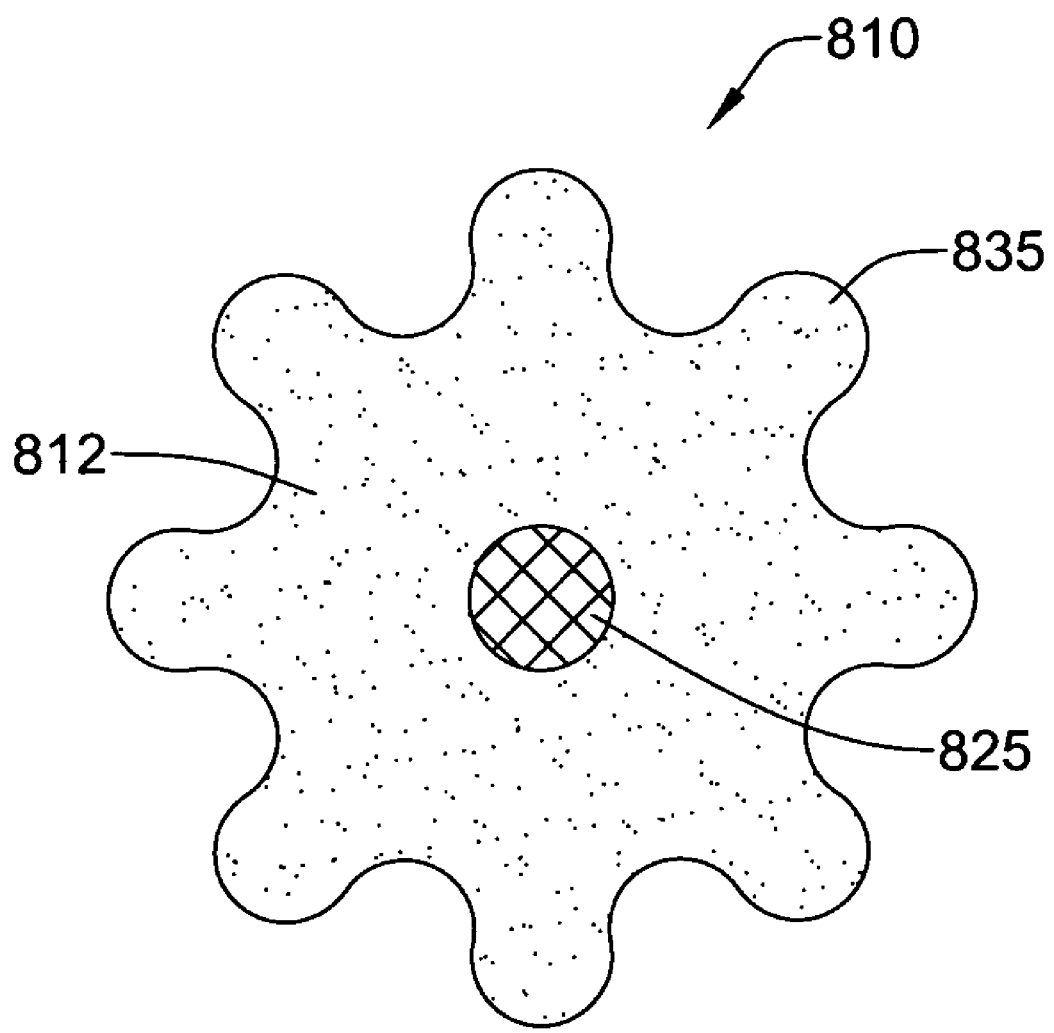
FIG. 15B is a cross-sectional view of the user-disposable member of FIG. 15A taken along line 15B-15B.

As shown in FIG. 15B, the member 810 may include a plurality of undulating portions or flutes 835 defined in the peripheral outer surface 822 of the member 810. The flutes 835 may be compressible and/or flexible to reduce the outer diameter of the member 810 in order to facilitate insertion of the member in an ear canal. For example slight rotation of the member 810, for example by manipulating the orientation of the core member 825 in a user's fingertips, in proximity to the ear canal may bias the flutes 835 in a folded over, or skewed position, thus decreasing the radial extents of the member 810. After insertion in the ear canal, the flutes 835 may attempt to return to their unbiased position. Therefore, the plurality of flutes 835 may allow the member 810 conform to the ear canal of a user.

Figure 16:
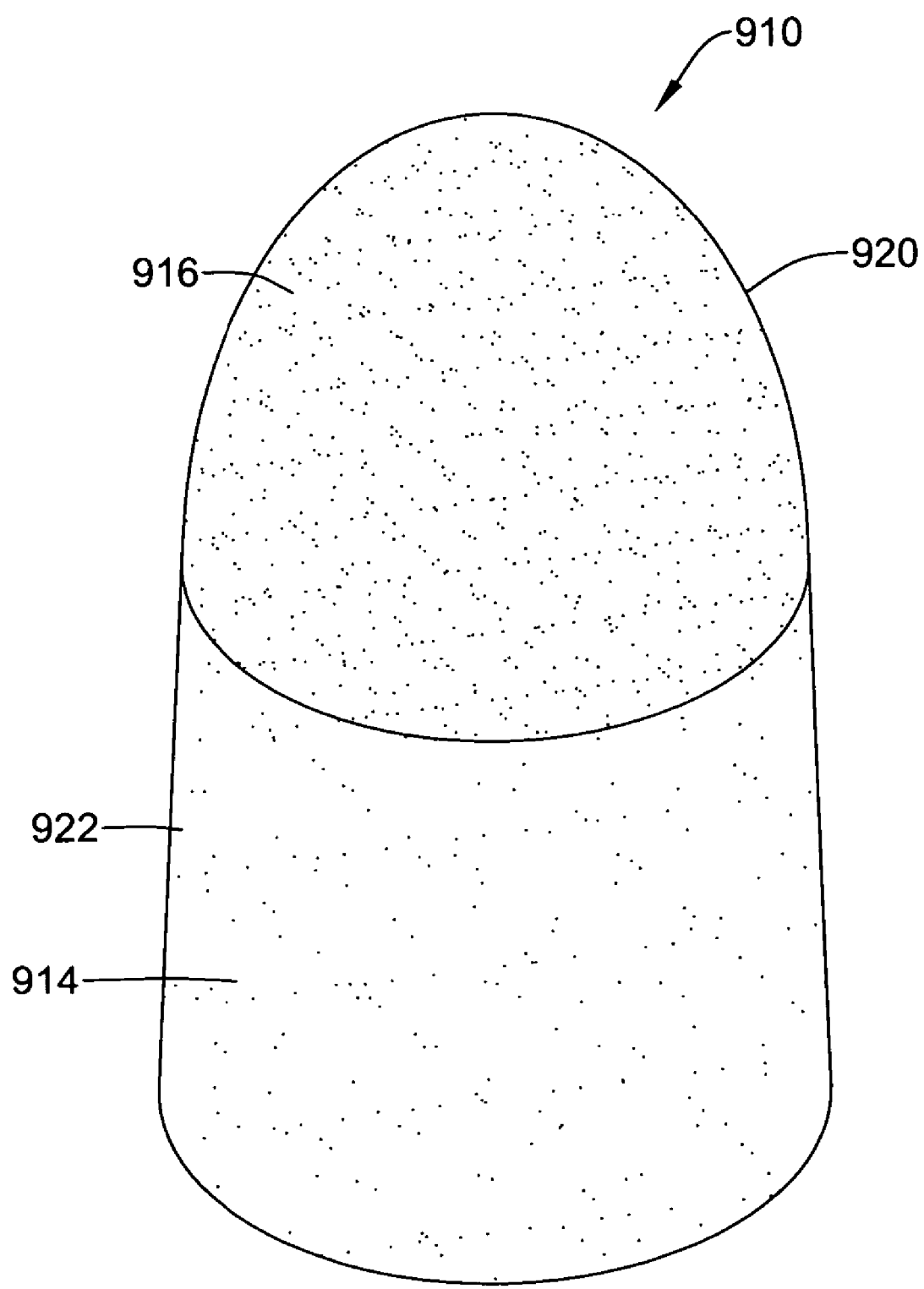
FIG. 16 is a perspective view a another illustrative embodiment of a user-disposable member.

Another exemplary embodiment, as shown in FIG. 16, may include a user-disposable member 910 having a more conical or bullet shape. The member 910 includes a first portion 914 having a peripheral outer surface 922 and a second portion 916 having a peripheral outer surface 920. The first portion 914 may be a frusta-conical shape and the second portion 916 may be a hemispherical shape converging with the frusta-conical shape of the first portion 914. The peripheral outer surface 920 of the second portion 916, or a portion thereof, may additionally have a coefficient of friction less than the coefficient of friction of the peripheral outer surface 922 of the first portion 914. For example, a portion of the peripheral outer surface 920 may be covered with a polymeric film providing lubricity to the second portion 916, or more proximal portion, of the member 910.

Figure 4:
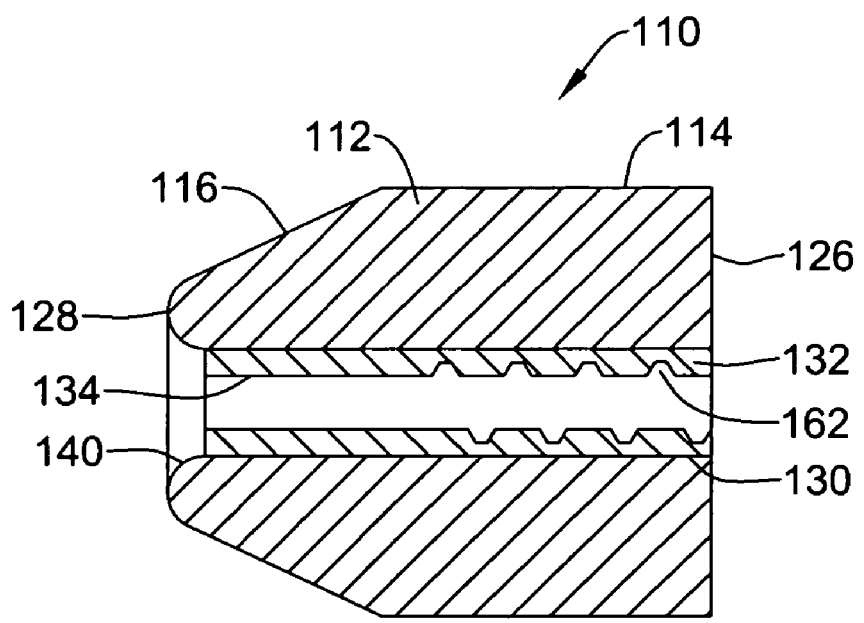
FIG. 4 is a cross-sectional view of the exemplary user-disposable member of FIG. 2.

FIG. 2 illustrates another embodiment of a user-disposable member 110, similar to the user-disposable member 10. The member 110 includes a first end 126 and a second end 128. The second end 128 may include a dimple or depression 140. In some embodiments, the depression 140 may be molded in the second end 128 during a molding process, such as in a molding process as discussed later herein. However, in other embodiments the depression 140 may be formed in an alternative process. The depression 140 may more readily be understood in FIG. 4. The depression 140 provides a soft tip at the second end 128 of the member 110. Additionally, the member 110 may include a lumen 130 extending from the depression 140 through the body 112 to the first end 126 of the member 110. The lumen 130 may be sized and/or configured to receive an elongate tubular member 132, as shown in FIG. 4. FIG. 4 is a cross-sectional view of the user-disposable member 110 of FIG. 2, wherein the lumen 130 and the elongate tubular member 132 may more readily be understood. As shown in FIG. 4, the second end 128 of the member 110 may extend beyond the elongate tubular member 132 in order to provide a more comfortable insertion portion of the member 110. The elongate tubular member 132 may include a lumen 134 extending therethrough. The elongate tubular member 132 may be secured to the member 110 by any suitable means. For example, in some embodiments the elongate tubular member 132 may be adhesively bonded to the lumen 130 of the member 110. In other embodiments, the elongate tubular member 132 may be thermally bonded to the lumen 130, or the elongate tubular member 132 may be affixed to the body 112 during the molding process. The elongate tubular member 132 may include a connecting portion for connecting the member 110 to a sound control device. As illustrated in FIG. 4, one such means may include a threaded portion 162 which may engage with a mating threaded portion of a connecting portion of a sound control device. Additional means for the coupling member 110 to a sound control device may include an interference fit or interlocking fit such as a ball-and-socket connection, a bayonet-type connection, adhesive, one or more grooves, or the like.

As illustrated in both FIGS. 2 and 4, the member 110, similar to the member 10, may include a first portion 114 and a second portion 116. The second portion 116 may be molded, for example, in a frusta-conical shape, or other shape as desired. The second portion 116 may include a peripheral outer surface 120 extending around the body 112 and located at a distance radially outward from the longitudinal axis of the body 112 of the member 110. The peripheral outer surface 120 may be a molded outer surface consequent molding the second portion 116 of the member 110. The second portion 116, or a portion thereof, may include a skin layer 118, which may be integrally formed during the molding process or during a subsequent process. The first portion 114 may include a generally cylindrical peripheral outer surface 122. The peripheral outer surface 122 may be a cut outer surface formed by cutting the member 110 from a polymeric foam sheet of material. The cut outer surface 122 may be free of, or devoid of, a skin layer such as the skin layer 118. Similar to the member 10, the outer surface 120 may have physical properties dissimilar to those of the outer surface 122. For example, the cut outer surface 122 may have a porosity greater than or less than the porosity of the molded outer surface 120, and/or the outer surface 122 may have a coefficient of friction greater than the coefficient of friction of the molded outer surface 120. In some embodiments, the cut outer surface 122 of foam material may include visible cut cellular membranes and the molded outer surface 120 may include substantially enclosed cellular membranes.

Figure 5:
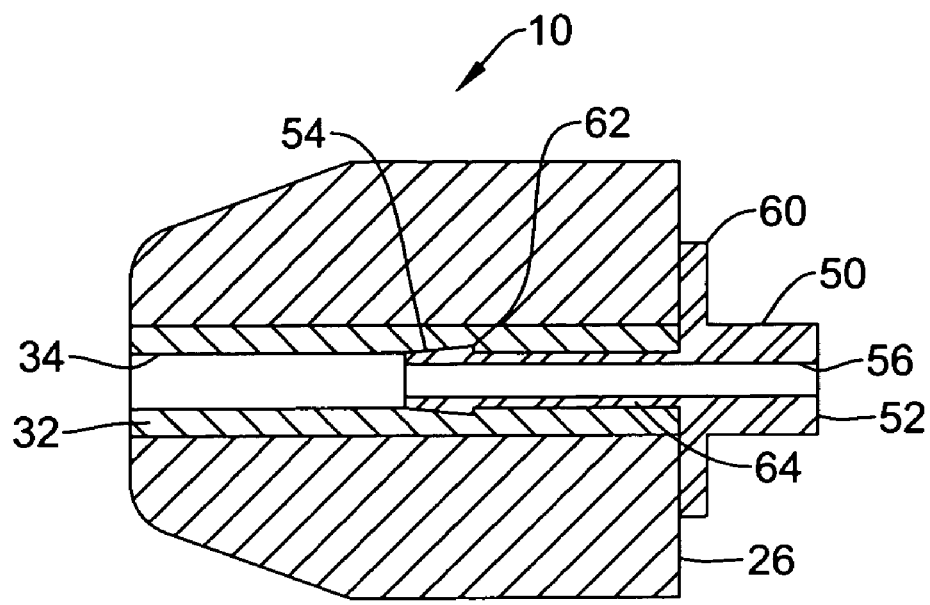
FIG. 5 is a cross-sectional view of the user-disposable member of FIG. 1 coupled to an exemplary connecting portion of a sound control device.

FIG. 5 is a cross-sectional view of the user-disposable member 10 coupled to an exemplary connector, such as the connecting portion 50 of a sound control device. The connecting portion 50 may include a proximal end 52, a distal end 54 and a lumen 56 extending therethrough. In some embodiments, the lumen 56 may define a sound tube for transmitting sound. The member 10 may be coupled to the connecting portion 50 of the sound control device. For example, the connecting portion 50 may include a means for connecting the member 10 to the connection portion 50 of a sound control device. For instance, a portion of the connecting portion 50 may include a ridge or burr 62 in the outer surface of the sound tube 64. The sound tube 64 may extend into or through the lumen 30 of the member 10. In embodiments where the member 10 includes the elongate tubular member 32, the sound tube 64 may extend into or through the lumen 34 of the elongate tubular member 32. Thus, the burr 62 may create an interference fit or interlocking fit between the sound tube 64 and the elongate tubular member 32. In other embodiments, the sound tube 64 may be devoid of a burr or other enlarged portion. In such an embodiment, the elongate tubular member 32 may fit snuggly over the outer surface of the sound tube 64 and/or be slightly stretched over the sound tube 64 in order to provide an interference or frictional fit between the inner surface of the elongate tubular member 32 and the outer surface of the sound tube 64. Additionally or alternatively, the connecting portion 50 may include a flange 60. Thus, the member 10 may be coupled to the connecting portion 50 such that the first end 26 of the member 10 abuts the flange 60.

One of skill in the art would recognize that the member 10 may be coupled to the connecting portion 50 by any other suitable means. For example, the member 10 may be adhesively bonded to the connecting portion 50 along a portion of the sound tube 64 and/or the flange 60. Other means may include another interference fit or interlocking fit such as a ball-and-socket connection, a threaded connection, a bayonet style connection, one or more ridges or grooves, a compression fit, or the like.

Figure 6:
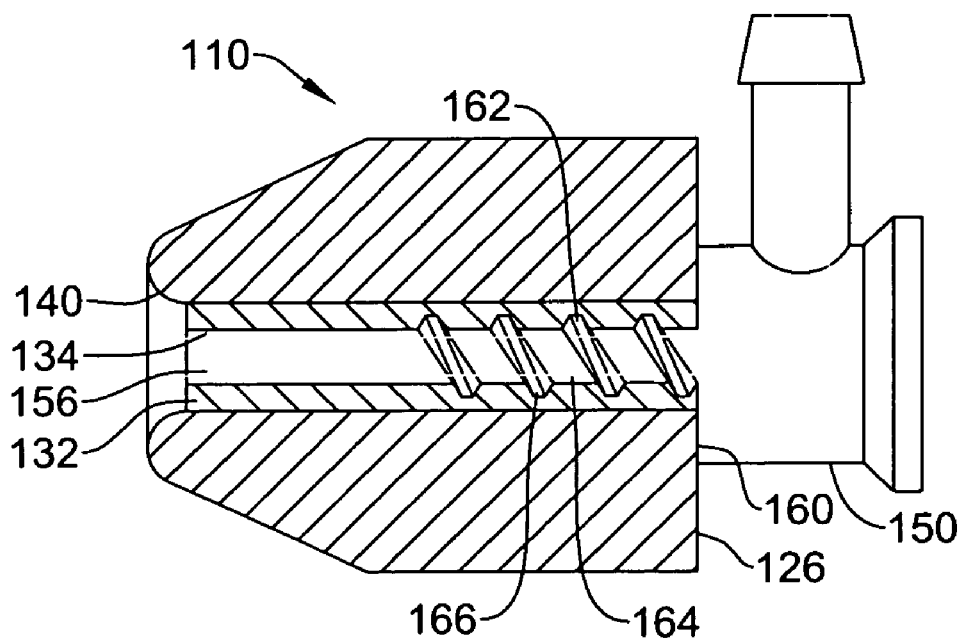
FIG. 6 is a cross-sectional view of the user-disposable member of FIG. 2 coupled to an exemplary connecting portion of a sound control device.

FIG. 6 is a cross-sectional view of the user-disposable member 110 coupled to an exemplary connector, such as a connecting portion 150. In the illustrative embodiment, the connecting portion 150 includes a sound tube 164 having a lumen 156 extending therethrough. The sound tube 164 may extend into or through the lumen 134 of the elongate tubular member 132. The user-disposable member 110 may be coupled to the connecting portion 150 in any desirable fashion. In some embodiments, the sound tube 164 may include a means for coupling the member 110 to the connecting portion 150, such as a threaded portion 166. The threaded portion 166 may mate with a threaded portion 162 of the elongate tubular member 132 to securely couple the member 110 to the connecting portion 150. In some embodiments, the member 110 may be coupled to the connecting portion 150 such that the first end 126 of the member 110 contacts the surface 160 of the connecting portion 150.

Figure 7:
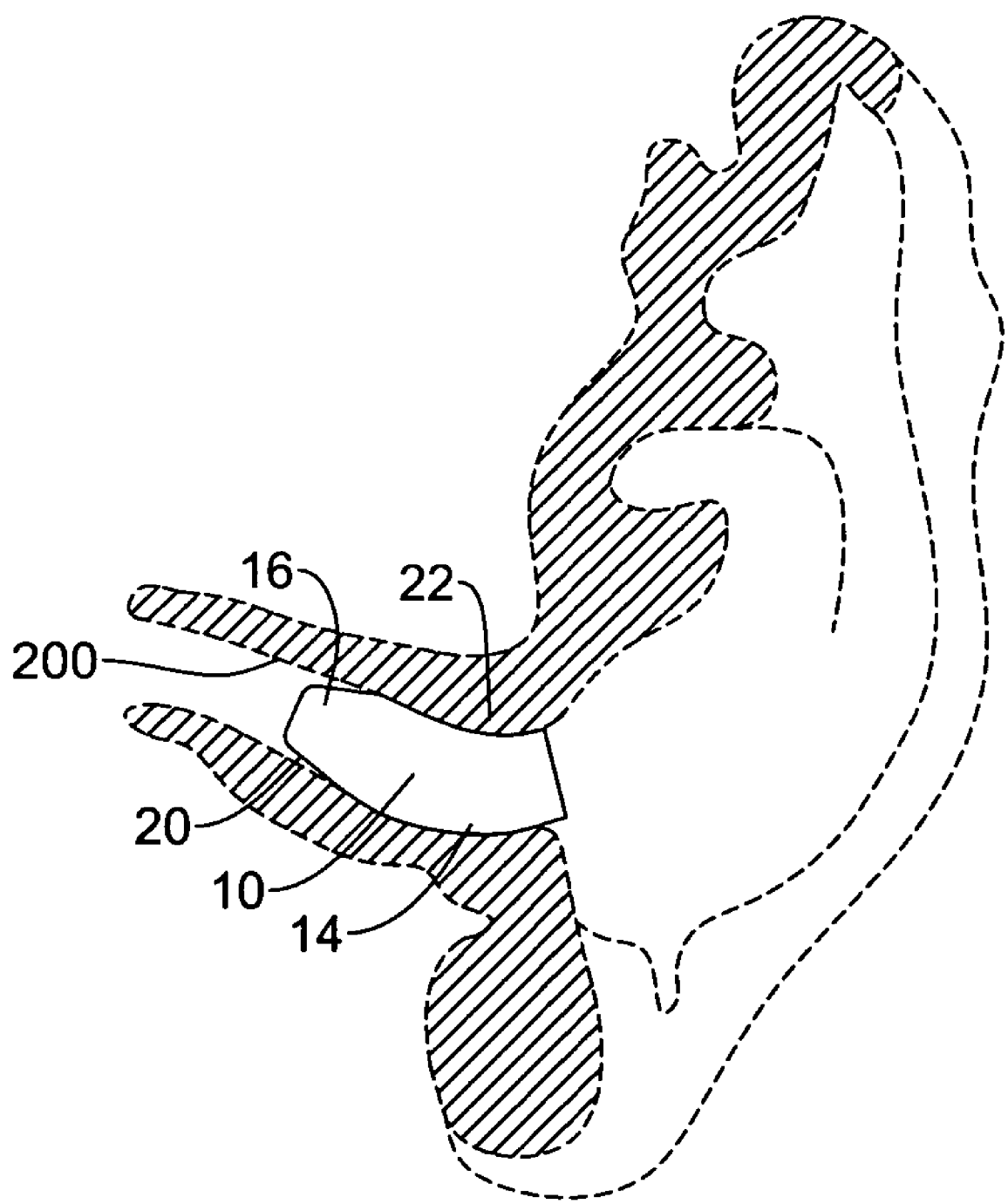
FIG. 7 is a cross-sectional view of an exemplary user-disposable member disposed in an ear canal.

FIG. 7 shows a user-disposable member, such as the user-disposable member 10 disposed in an ear canal 200. The member 10 may be compressed into a relatively low profile and then inserted into the ear canal 200. As the second portion 16 may be the more distal portion, or the leading portion, of the member 10, the coefficient of friction of the peripheral outer surface 20 of the second portion 16 may facilitate insertion of the member 10 into the ear canal 200. As the member 10 expands to attempt to return to its original dimensions, the peripheral outer surface 22 of the first portion 14, or more proximal portion, may contact and conform to the inner surface of the ear canal 200. The coefficient of friction of the peripheral outer surface 22 may provide sufficient retention to retain the member 10 firmly within a portion of the ear canal 200. As shown, the cross section of the ear canal indicates the presence of bends that will vary in degree from individual to individual.

Figure 8:
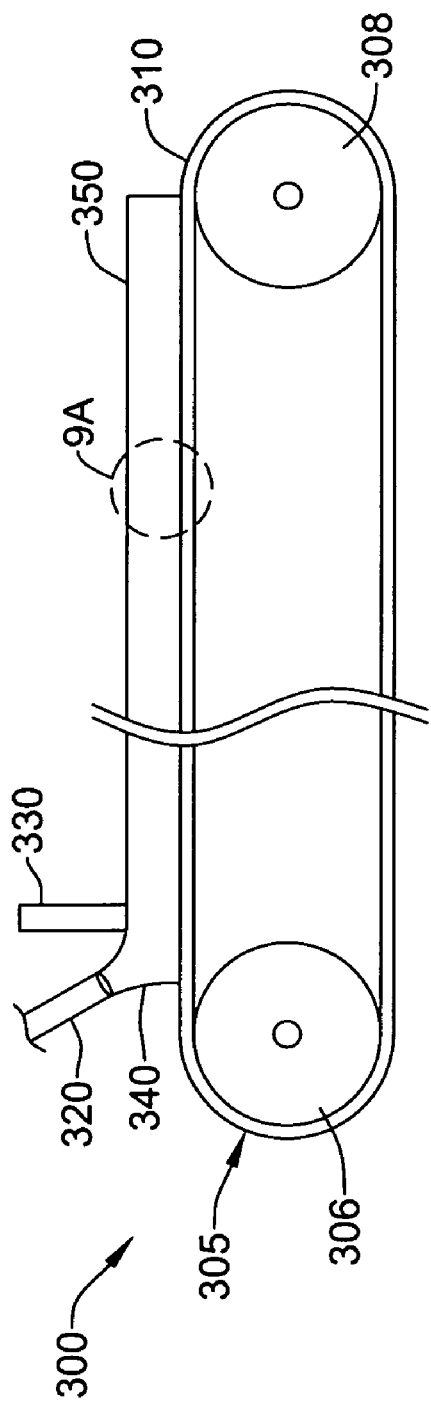
FIG. 8 is a plan view of exemplary manufacturing apparatus for forming a user-disposable member.

An exemplary method of forming a user-disposable member such as the member 10 will now be described. As shown in FIG. 8, the user-disposable members 10 maybe formed during a continuous foam forming process. Such a process may include a conveyor system 300 including a conveyor 305 having a moving surface 310 shown generically in FIG. 8. Although a conveyor 305 having a continuous belt 310 extending between two rotating drums 306, 308 is shown in FIG. 8, other equipment having a moving surface may be used. The conveyor system 300 may include an injector 320 for injecting or pouring a polymeric material 340 onto the continuous surface 310 and a leveling device such as a knife 330 to level the polymeric material 340. The thickness of the polymeric material 340 may be precisely controlled by adjusting the leveling device 330 to a desired position and/or metering the amount of polymeric material 340 disposed on the continuous surface 310. The polymeric material 340 may travel on the continuous surface 310 beyond the leveling device 330 as the continuous surface 310 is moving. The polymeric material 340 may be cured into a polymeric foam material 350 during a curing process. Controlling the thickness and/or properties of the polymeric material 340 enables a layer of polymeric foam material 350 to be formed to a desired thickness. In some embodiments, an additional or alternative leveling device may be provided to subject the polymeric foam material 350 to a desired thickness. Such a process may be used to form a layer of polymeric foam material 350 of any suitable dimensions.

Figure 9B:
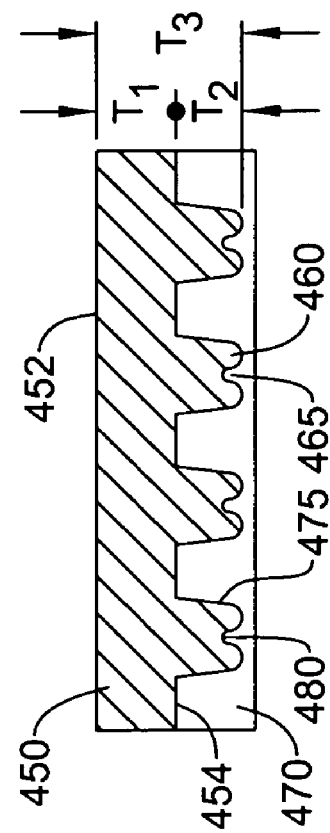
FIG. 9B is a cross-sectional view of a portion of an alternate exemplary manufacturing apparatus.
Figure 9A:
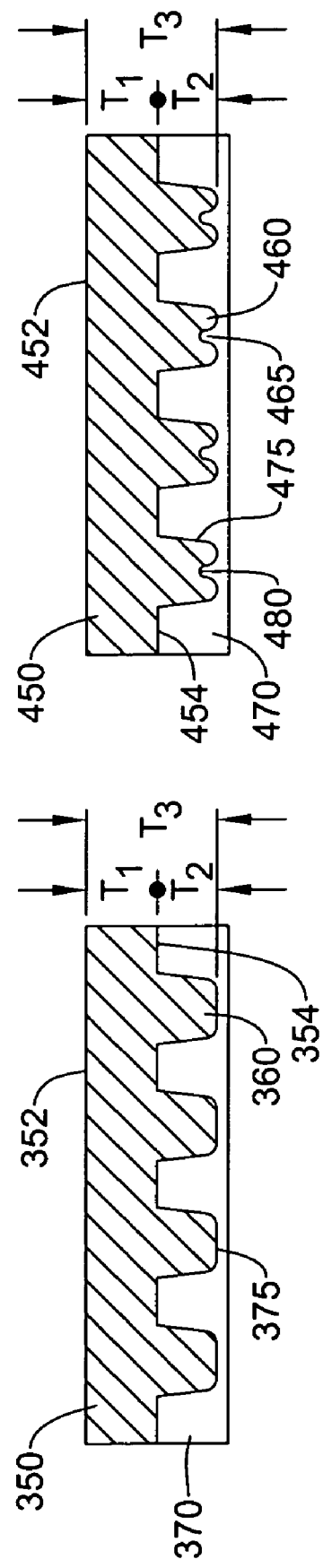
FIG. 9A is a cross-sectional view of a portion of an exemplary manufacturing apparatus.

FIG. 9A shows an enlarged cross-sectional view of a portion of the conveyor system 300. The conveyor system 300 may include a mold 370 having one or more, or a plurality of cavities 375. The mold 370 may be an integral portion of the continuous surface 310, or the mold 370 may be a separate portion coupled to or disposed on the continuous surface 310. The mold 370 may be disposable after a single use or a few uses, or the mold 370 may be formed to be repeatedly used for an extended period. A polymer material 340 may be injected or poured onto the mold 370 and into the cavities 375. Thus, a layer of polymeric foam material 350 may be formed on the mold 370. The polymeric foam material 350 may include a continuous layer having a thickness $T_1$ defined between a first side 352 and a second side 354. The thickness of the continuous layer may be controlled during operation. The first side 352 may include a generally planar surface and the second side 354 may include a plurality of projections 360 extending from the second side 354. The projections 360 generally correspond to and reflect the cavities 375 of the mold 370. The cavities 375 may have a depth, and thus the projections 360 may have a height $T_2$ substantially equivalent to the depth of the cavities 375. Therefore, the continuous polymeric foam material 350 may have an overall thickness $T_3$ greater than the height of the projections 360. In some embodiments, the projections 360 may have a molded outer surface which may include a skin layer integrally formed during a molding process. A skin layer on the projections 360 may also be formed on the projections 360 through a chemical, thermal or mechanical treatment of the projections 360 subsequent a molding process or as an additional layer applied to the projections 360. The projections 360 having a molded outer surface may form the portion of a user-disposable member including a molded outer surface, after removal from the polymeric foam layer 350 as discussed herein. The polymeric foam layer 350 may be separated from the mold 370 subsequent the molding process. In one alternative embodiment, a film could first be formed in the mold or a film former placed therein.

FIG. 9B shows an enlarged cross-sectional view of a portion of the conveyor system including an alternative mold 470. The mold 470 includes a plurality of cavities 475 having an alternative cross-section. The cavities 475 may include a protuberance 480. The continuous layer of polymeric foam 450 includes a first side 452 and a second side 454. The first side 452 may be a planar surface, and a plurality of projections 460 may extend from the second side 454. The projections 460 may include a depression 465 formed in the projection 460 as a result of the protuberance 480 in the cavity 475 of the mold 470. The depression 465 may substantially be the dimple 140 of the user-disposable member 110. Cavities of different dimensions and arrangements may be used to create projections of any desired extent projecting from the continuous foam layer 450.

Figure 10:
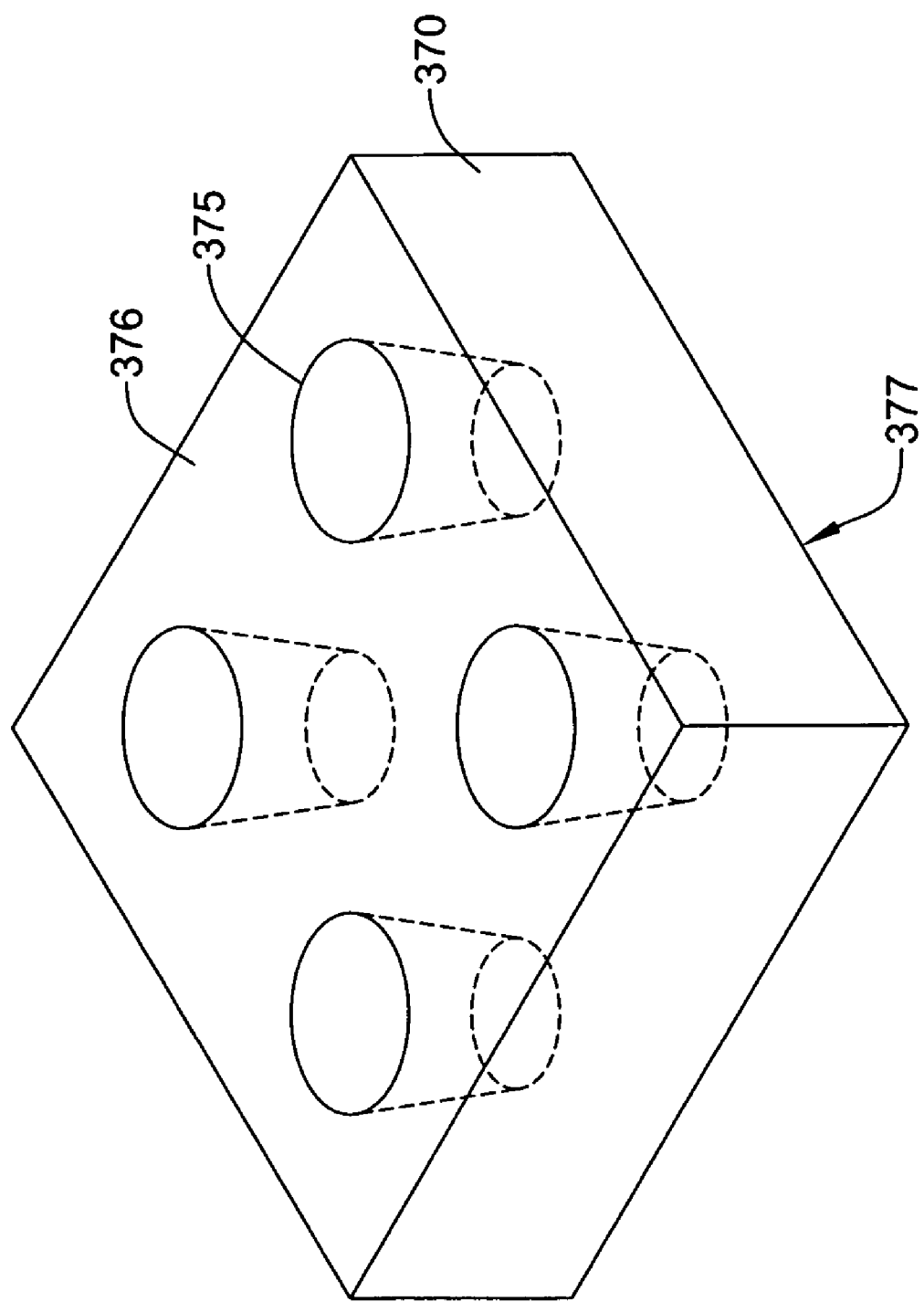
FIG. 10 is a perspective view of a portion of an exemplary mold.

An enlarged portion of the mold 370 is shown in FIG. 10. The mold 370 may include a first surface 376, a second surface 377 and a plurality of cavities 375 extending into the mold 370. The cavities 375 may be arranged in a regular pattern as shown in FIG. 10, or the cavities 375 may be randomly arranged. The cavities 375 may be disposed in an array, such as the two-by-two array shown in FIG. 10. However, the mold 370 may include an array of cavities 375 of any desired proportions, such as a ten-by-fifty array, a twenty-by-two hundred array, or a fifty-by-one thousand array. The cavities 375, shown in FIG. 10, have a frusta-conical shape. However, cavities 375 may have any other geometric shape as desired. For example, the cavities 375 could be bulbous, spherical, hemispherical, cylindrical, or other desired shapes.

Figure 11:
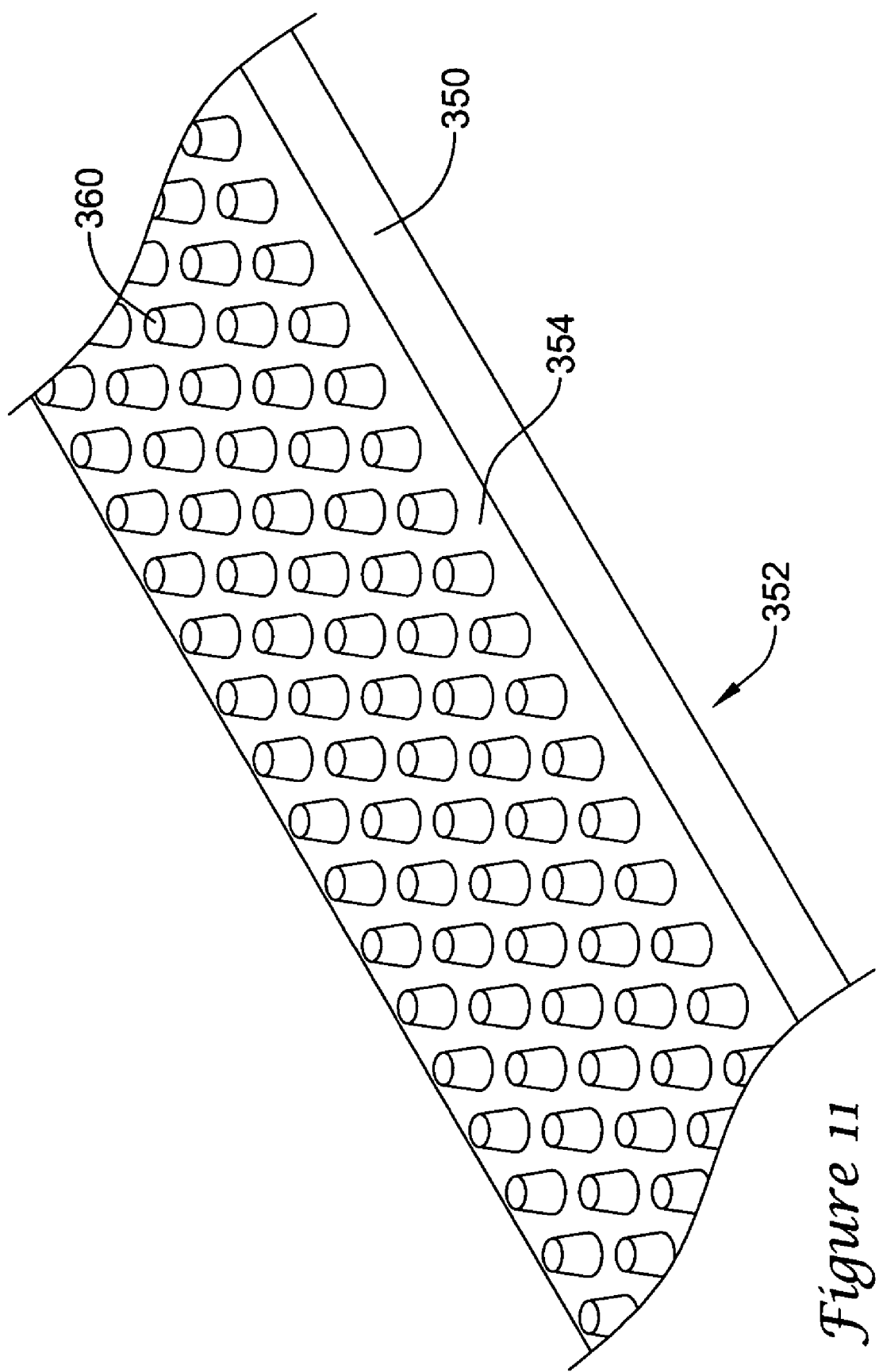
FIG. 11 is a perspective view of a portion of a sheet of polymeric foam material.

FIG. 11 shows a portion of a continuous polymeric foam layer 350 formed using a mold such as the mold 370 illustrated in FIG. 10. The polymeric foam layer 350 includes a first side 352 and a second side 354. The first side 352 may include a substantially planar surface and the second side 354 may include a plurality of projections 360 extending therefrom. The projections 360 may be arranged in a regular pattern or randomly located on the second side 354 and extending therefrom. The arrangement of the cavities 375 of the mold 370 dictates the arrangement of the projections 360 of the foam layer 350. As shown in FIG. 11, the projections 360 may be arranged in an array of any suitable dimensions. Although the projections 360 are shown to be spaced apart from each other, the projections 360 may be positioned much closer to one another on the foam layer 350 in order to optimize manufacturing productivity and/or reduce material waste. The projections 360 may include a molded outer surface from a molding process. As discussed above, in some embodiments the projections 360 may include a skin layer on a molded outer surface.

Figure 12B:
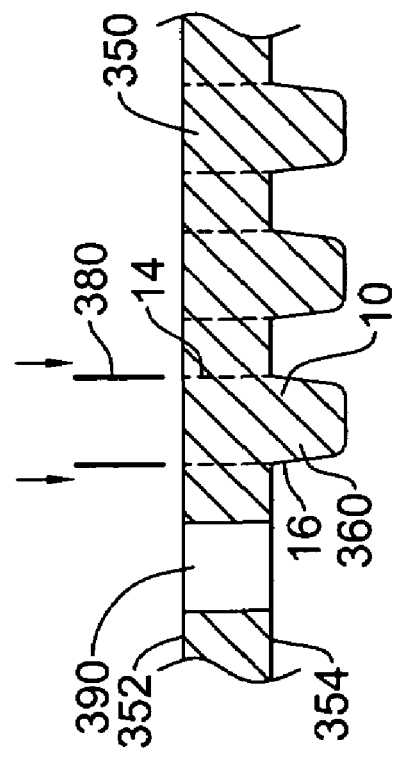
FIG. 12B is a cross-sectional view of a process of removing an alternate embodiment of a user-disposable member from a sheet of polymeric foam material.
Figure 12A:
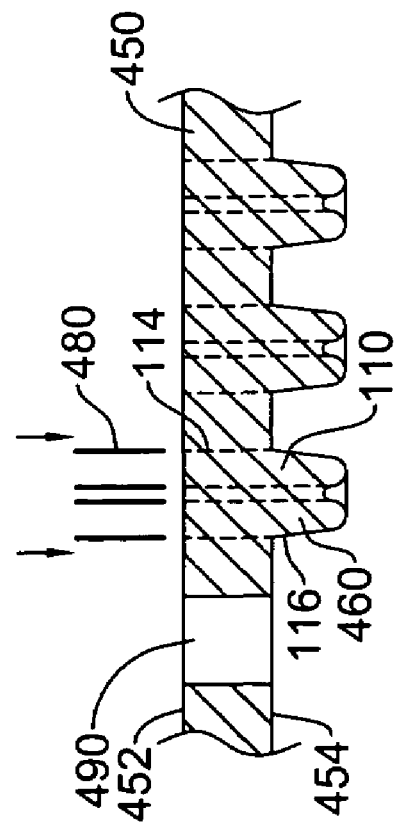
FIG. 12A is a cross-sectional view of a process of removing a user-disposable member from a sheet of polymeric foam material.

A process of forming user-disposable members such as the members 110 from a continuous foam layer such as the foam layer 450 is illustrated in FIG. 12A. A cutting device 480 may be positioned generally aligned with a projection 460 in the foam layer 450. FIG. 12A illustrates the cutting device 480 adjacent the first, generally planar side 452 of the foam layer 450. However, in other embodiments the cutting device 480 may be positioned substantially adjacent to the second side 454. Arrows in FIG. 12A generally demonstrate the cutting device 480 separating the member 110 from the remainder of the foam material 450. Thus, the member 110, shown with dashed lines in FIG. 12A may be cut from the foam layer 450. The member 110 may be cut from the polymeric foam material 450 by any suitable cutting technique, such as die cutting, punching, laser cutting, or the like. Dashed lines in FIG. 12A illustrate the cut portion of the foam layer 450. The member 110 may additionally have a central lumen also shown in dashed lines cut therethrough during the cutting process or during an additional cutting process. As a result of the cutting process, the member 110 includes a first portion 114 cut from the foam layer 450 and a second portion 116 including the projection 460 extending from the cut portion. It can be seen from this process that the first portion 114 of the member 110 may have a cut peripheral outer surface 122 and the second portion 116 may have a molded peripheral outer surface 120.

The cutting process may include multiple cutting devices 480 positioned such that multiple members 110 may be cut from the foam material 450 simultaneously or sequentially. FIG. 12A shows a space 490 from which a member 110 has previously been removed from the foam material 450. A large quantity of user-disposable members 110 may be manufactured as necessary from a continuous layer of foam 450 subjected to multiple cutting devices 480.

Another process of removing a user-disposable member 10 from a polymeric foam material 350 is illustrated in FIG. 12B. A cutting device 380 may be generally aligned with the projection 360 in the foam layer 350. The member 10, illustrated with dashed lines, may be removed from the foam layer 350 by die cutting, punching, laser cutting, or the like. The member 10 may include a first portion 14 having a cut peripheral outer surface 22 corresponding to the dashed lines of FIG. 12B where the member 10 is separated from the foam layer 350. Additionally, the member 10 may include a second portion 16 having a molded peripheral outer surface 20. The second portion 16 may substantially include the projection 360 of the foam layer 350. FIG. 12B shows a space 390 from which a member 10 has previously been removed from the foam material 350.

Figure 13:
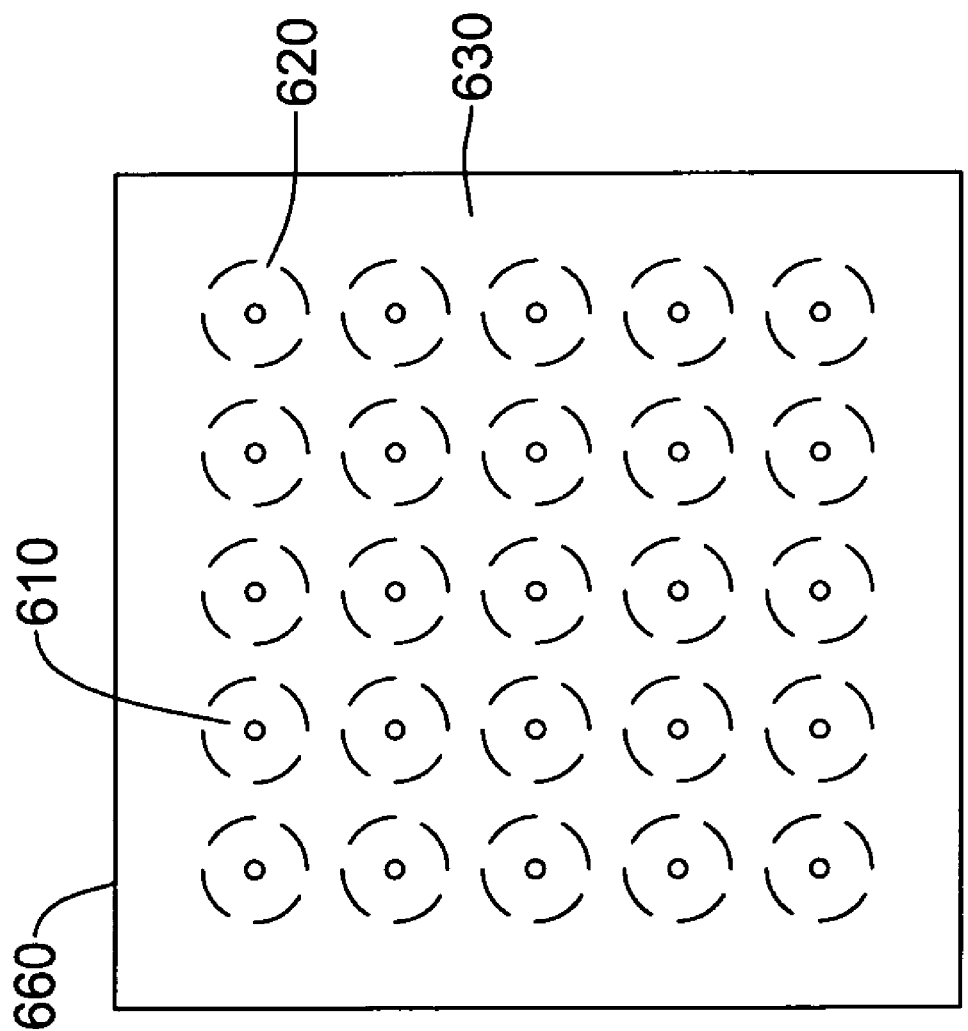
FIG. 13 is a plan view of a sheet of polymeric foam having a plurality of pre-cut user-disposable members.

FIG. 13 shows a top view of a section of a polymeric foam material or pad 660 having a plurality of user-disposable members 610 pre-cut in the pad 660. The user-disposable members 610 may be similar to the members 10, 110, or the members 610 may be dissimilar. The members 610 may be cut such that small uncut wing portions or bridges 620 retain the members 610 attached to the surrounding waste portion or "weed" 630 of the pad 660. As shown in FIG. 13, each member 610 may be connected to the weed 630 by four bridges 620. However, in other embodiments, one, two, three, four, or more bridges 620 may be used to secure the members 610 to weed 630.

The pad 660 may provide a supply of user-disposable members 610. An individual member 610 may be removed from the pad 660 when desired by applying sufficient force to separate the member 610 from the weed 630 at the bridges 620. The pad 660 may be used to package the members 610 for use in a given application. The pad 660 may include any number of user-disposable members 610 pre-cut from a polymeric foam layer, as desired.

In one alternative embodiment, the foam member can be produced by the lamination of two or more different foams. For example the foam member may include a first layer of material and a second layer of material. The first layer of material may provide an outer surface with a first coefficient of friction, and the second layer of material may provide an outer surface with a second coefficient of friction. The first coefficient of friction may be greater than the second coefficient of friction. Thus, in some embodiments, the second layer of material may provide the user-disposable member with a lower coefficient of friction for the second portion, and the first layer of material may provide the user-disposable member with a higher coefficient of friction for the first portion. The portions could be affixed to one another by adhesive means, such as a double coated medical adhesive tape from 3M, a tying material, such as a polymeric material, adhesive, resin, or other bonding material or layer for affixing the first portion to the second portion. The second portion could also include a substantive lubricant thereon which is restricted from the first portion by the adhesive tape. The lubricant may give the peripheral outer surface of the second portion a lower coefficient of friction than the peripheral outer surface of the first portion. A preferred lubricant stays on the second portion during insertion and does not come off to coat the ear canal which would adversely affect retention.

Figure 17:
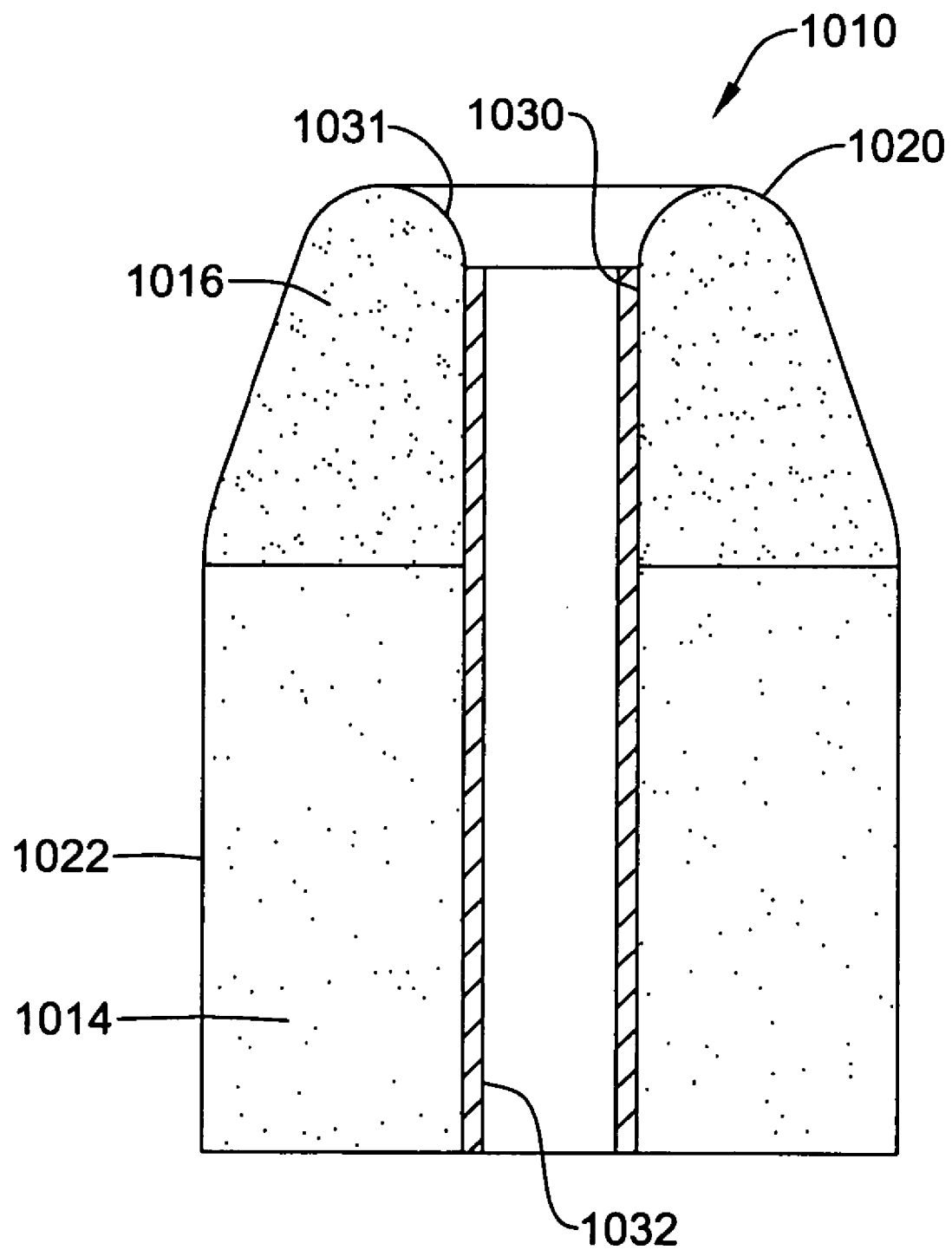
FIG. 17 is a cross-sectional view of another illustrative embodiment of a user-disposable member.

One such exemplary embodiment is illustrated in FIG. 17. The user-disposable member 1010 includes a first portion 1014 comprising a first polymeric foam material and a second portion 1016 comprising a second polymeric foam material different from the first material. The first portion 1014 includes a peripheral outer surface 1022 having a coefficient of friction, and the second portion 1016 includes a peripheral outer surface 1020 having a coefficient of friction greater/less from that of the outer surface 1022 of the first portion 1014. For example, the coefficient of friction of the outer surface 1020 of the second portion 1016 may be less than the coefficient of friction of the outer surface 1022 of the first portion 1014. In some embodiments, the member 1010 may include a lumen 1030 extending through the member 1010 and an elongate tubular member 1032 positioned in the lumen 1030 and affixed to the body of the member 1010. FIG. 17 also illustrates, as with FIG. 4, a dimple or indentation 1031, creating a soft distal tip.

In a multilayered foam piece, insertion force can also be controlled by including a second portion made from a foam having a low compressional modulus. The low modulus portion gives the distal portion an effective coefficient of friction (ease of insertion) with out the addition of a layer or skin. Exemplary foams can include Elastic Nolatex or Swisstex SAF 6060.

Figure 18B:
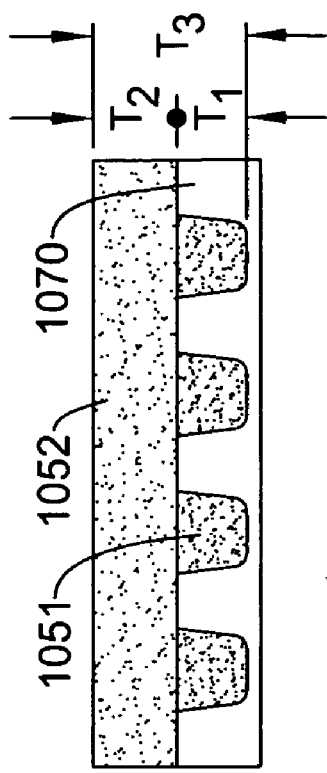
FIGS. 18A-18C are cross-sectional views illustrating an exemplary process in the manufacture of the user-disposable member of FIG. 17.
Figure 18A:
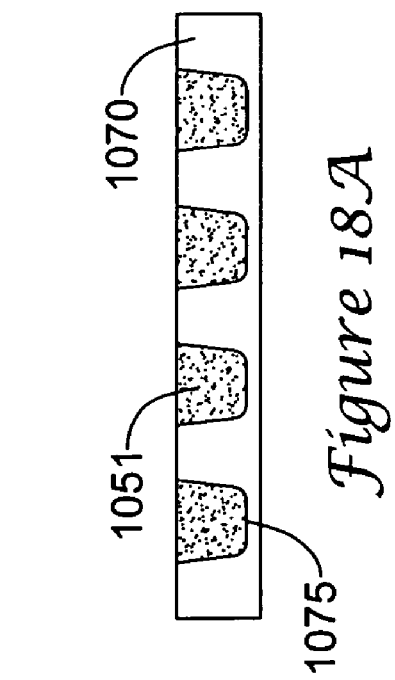
Figure 18C:
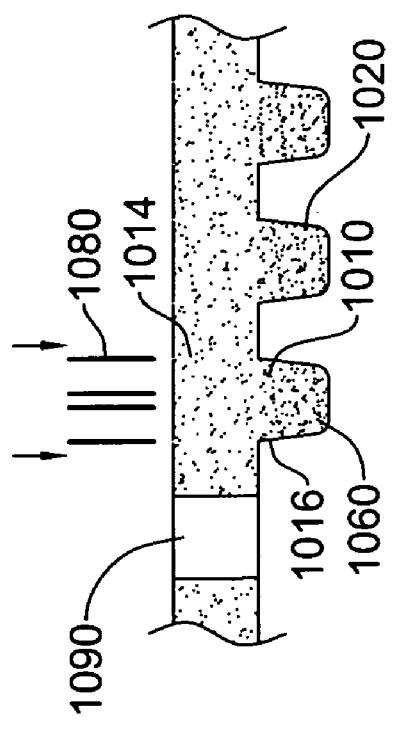

FIGS. 18A-18C illustrate an exemplary method of forming a multilayered user-disposable member, such as the member 1010 illustrated in FIG. 17. A first layer of polymeric material is poured or otherwise placed in the mold 1070. For example, the mold 1070 may include a plurality of cavities 1075, and the first layer of polymeric material may be poured into the cavities 1075 of the mold 1070. In a subsequent step, a second layer of polymeric material dissimilar from the first polymeric material may be poured or otherwise placed on top of the first layer of polymeric material. In some embodiments, the second polymeric material may be placed on top of the first layer of material after the first layer of polymeric material has had sufficient time to cure into a polymeric foam material 1051. However, in other embodiments, the second layer of polymeric material may be placed on top of the first layer of material prior to curing the material, thus both layers of material may be cured simultaneously. Nevertheless, upon curing of the materials, two layers of polymeric foam material differing in properties may be formed. A first layer of polymeric foam material 1051 may be formed and a second layer of polymeric foam material 1052 dissimilar from the first layer of polymeric foam material 1051 may be formed adjacent to the first layer of polymeric foam material 1051. In some embodiments, a tie layer or other bonding layer may be disposed between the first polymeric foam layer 1051 and the second polymeric foam layer 1052 to facilitate bonding the two layers together.

Thus, the formed multilayer polymeric material may comprise a first layer of material 1051 having a thickness, $T_1$, and a second layer of material 1052 having a thickness, $T_2$. Thus, the entire thickness of the multilayer polymeric material may have a thickness, $T_3$, having two or more dissimilar layers of polymeric material. Although the first layer of material 1051 is illustrated as having a thickness, $T_1$, generally corresponding to the depth of the cavities 1075, in other embodiments, the thickness, $T_1$, of the first layer of material 1051 may be less than or greater than the depth of the cavities 1075. Thus, in other embodiments, the second layer of material 1052 may extend into the cavities 1075, or the second layer of material 1052 may have a reduced thickness from that illustrated.

As shown in FIG. 18C, user-disposable members, such as the user-disposable members 1010 may then be cut, punched, or otherwise removed form the multilayered polymeric foam material. A cutting device 1080 may be generally aligned with the projection 1060 of the multilayered foam material. The member 1010, illustrated with dashed lines, may be removed from the multilayered foam material by die cutting, punching, laser cutting, or the like. Thus, the member 1010 may include a first portion 1014 having a peripheral outer surface 1022 being a cut outer surface corresponding to the dashed lines of FIG. 12B where the member 1010 is separated from the remainder of the multilayered foam material. Additionally, the member 1010 may include a second portion 1016 having a peripheral outer surface 1020 being a molded outer surface. The second portion 1016 may substantially include the projection 1060 of the multilayered foam material formed from the cavities 1075. FIG. 18C shows a space 1090 from which a member 1010 has previously been removed from the multilayered foam material.

Figure 19:
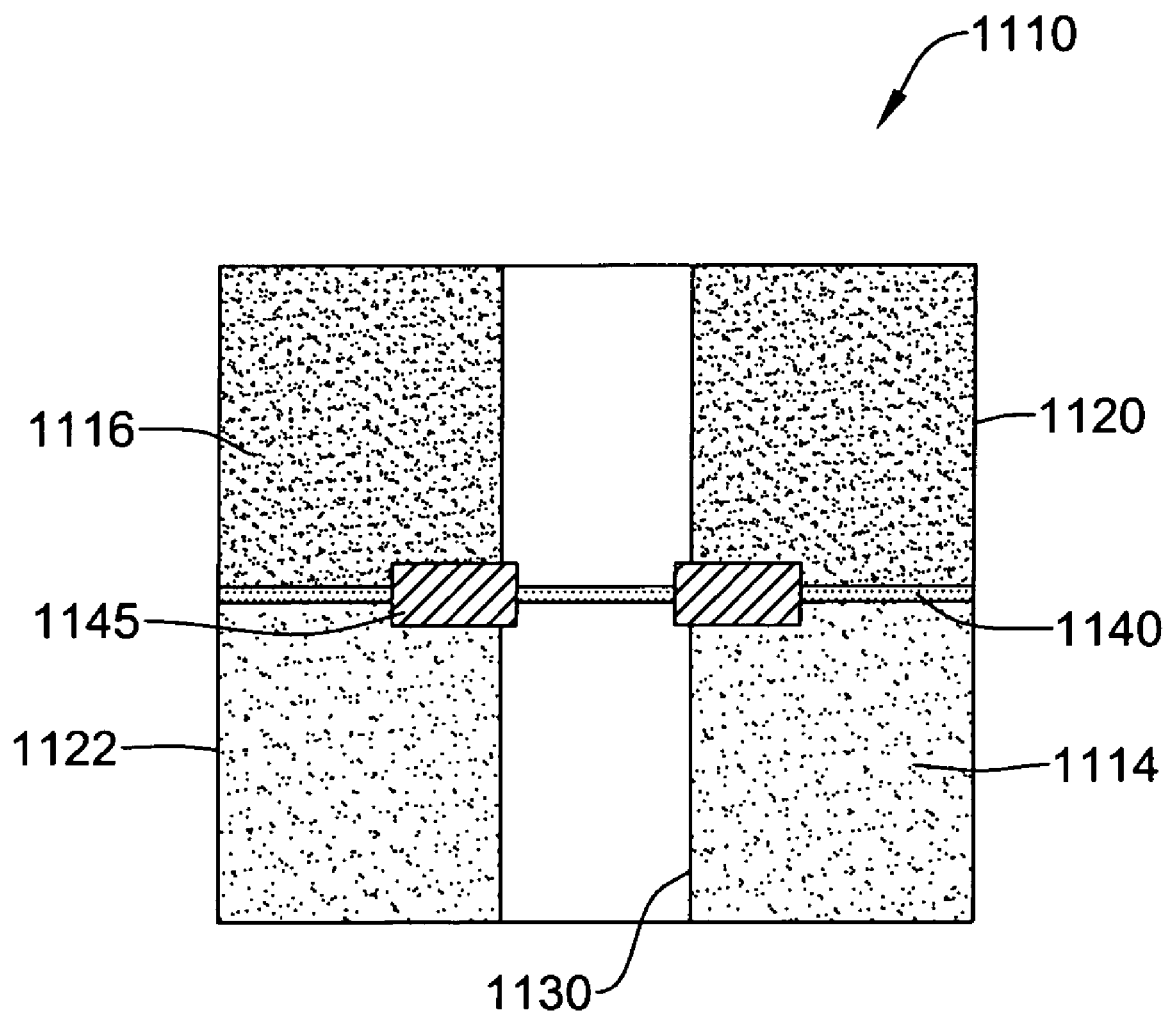
FIG. 19 is a cross-sectional view of another illustrative embodiment of a user-disposable member.

Another multilayered user-disposable member is shown in FIG. 19 as the user-disposable member 1110. The member 1110 includes a first layer of material 1114, which may be a polymeric foam material, and a second layer of material 1116, which may be a polymeric foam material, dissimilar to the first layer of material 1114. For example, the second layer of polymeric foam material 1116 may have a dissimilar porosity than the porosity of the first layer of polymeric foam material 1114. For instance, the porosity of the first layer of material 1114 may be less than the porosity of the second layer of material 1116. Although the member 1110 is illustrated as including two dissimilar layers affixed together, in other embodiments, the member 1110 may include three or more layers of dissimilar materials. The first layer of material 1114 may be affixed to the second layer of material 1116 by any desired means. For example, as illustrated in FIG. 19, the first layer 1114 may be affixed to the second layer 1116 by a bonding layer 1140 the bonding layer 1140 may be an adhesive, resin, tying material, or other substance conducive to affixing the first layer 1114 to the second layer 1116. A coating or skin on the surface can also be included.

The first layer of material 1114 includes a peripheral outer surface 1122. For example, in the illustrative embodiment the first layer of material 1114 may be a cylindrical layer of material having a cylindrical peripheral outer surface 1122. However, in other embodiments the first layer of material 1114 may be of other desired shapes. The outer surface 1122 of the first layer of material 1114 may have a first coefficient of friction. The second layer of material 1116 includes a peripheral outer surface 1120. For example, in the illustrative embodiment the second layer of material 1116 may be a cylindrical layer of material having a cylindrical peripheral outer surface 1120. However, in other embodiments the second layer of material 1116 may be of other desired shapes.

In forming the user-disposable member 1110, a first sheet of polymeric foam material comprising the first material may be affixed to a second sheet of polymeric foam material comprising the second material such as by the bonding layer 1140, forming a multilayer laminated material. Having formed a multilayered polymeric foam material, individual user-disposable members 1110 may then be cut, punched, or otherwise separated from the multilayer laminated material.

In some embodiments, such as the embodiment illustrated in FIG. 19, the user-disposable member 1110 may include an annular ring 1145 disposed at one end or disposed within the member 1110. For example, the annular ring 1145 may be disposed between the dissimilar layers of material. The annular ring 1145 may facilitate coupling the member 1110 to a connecting portion of a sound control device. For example, a portion of a sound control device may be inserted through the lumen 1130 of the member 1110. The annular ring 1145 may be configured to mate with a groove or recess in the outer surface of the connecting portion inserted through the lumen 1130. Thus, the annular ring 1145, mated with the groove or recess of the connecting portion of a sound control device may provide sufficient retention of the member 1110 to prevent premature separation of the member 1110 from the sound control device.

Figure 20:
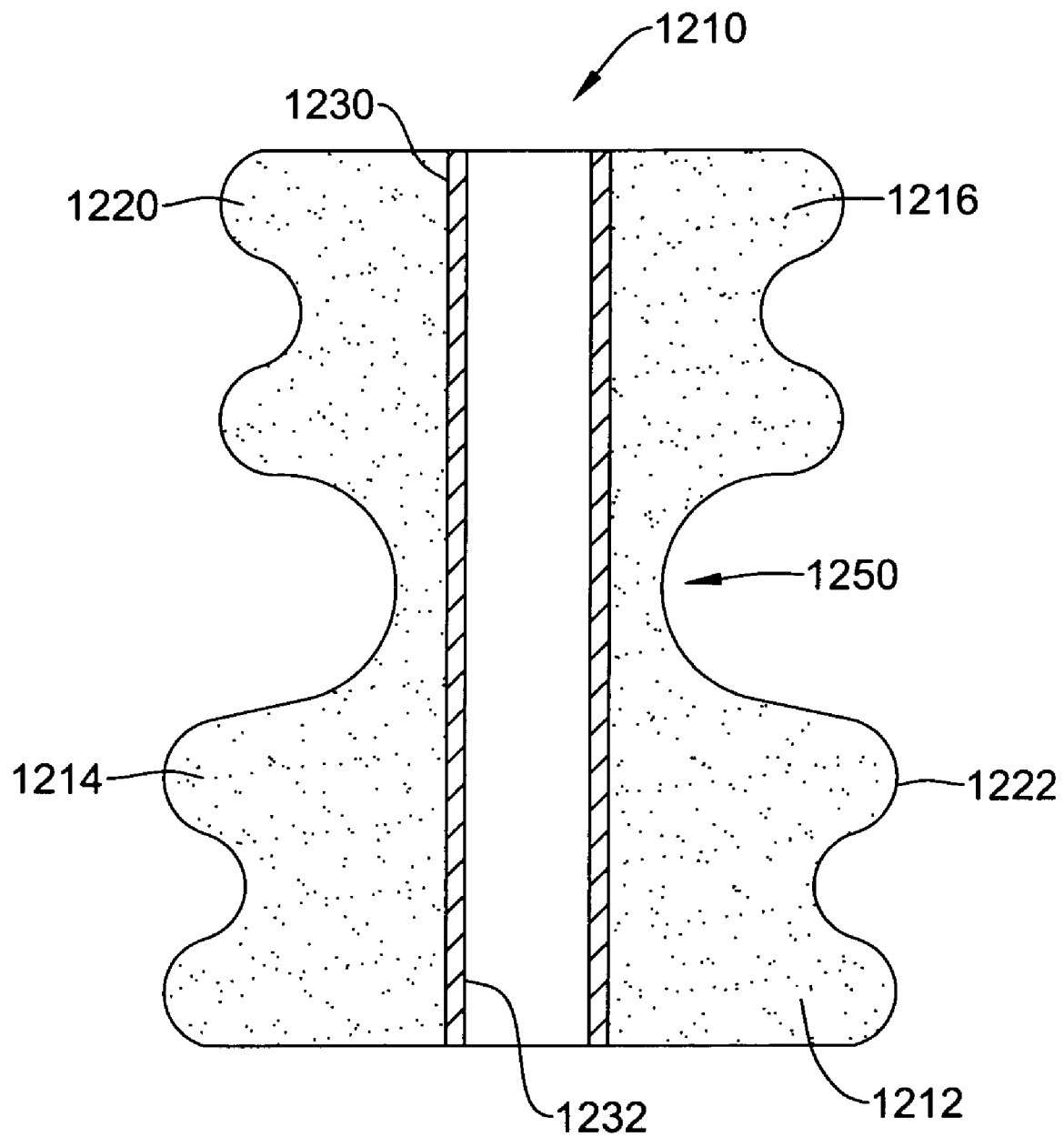
FIG. 20 is a cross-sectional view of another illustrative embodiment of a user-disposable member.

Another embodiment of a user-disposable member is illustrated in FIG. 20. The user-disposable member 1210 includes a polymeric foam body 1212 including a first portion 1214 and a second portion 1216. The first portion 1214 may be any desired shape. For example, as illustrated in FIG. 20, the first portion 1214 may have an apple core shape including a plurality of ridges. However, in other embodiments the first portion 1214 may have any other desired shape, such as bulbous, spherical, hemispherical, conical, cylindrical, or the like. The second portion 1216 may also be of any desired shape. For example, as illustrated in FIG. 20, the second portion 1216 may have an apple core shape including a plurality of ridges. However, in other embodiments the second portion 1216 may have any other desired shape, such as bulbous, spherical, hemispherical, conical, cylindrical, or the like.

The member 1210 includes a reduced periphery portion between the first portion 1214 and the second portion 1216 which may be considered a flexibility region 1250. The flexibility region 1250 may increase the flexibility of the member 1210 between the first portion 1214 and the second portion 1216. Thus, the member 1210 may readily conform to the curvature of the ear canal of a user, for example, the first bend of the ear canal.

The member 1210 may additionally include an elongate tubular member 1232, such as a polymeric tubular member, positioned and/or affixed to the lumen 1230 of the body 1212 of the member 1210. The elongate tubular member 1232 may provide the member 1210 with sufficient rigidity, yet allow sufficient flexibility for insertion into a user's ear canal. The elongate tubular member may be formed of a latex material, such as a coating formed on a mandrel.

The first portion 1214 includes a peripheral outer surface 1222 and the second portion 1216 includes a peripheral outer surface 1220. The peripheral outer surface 1220 of the second portion 1216 may have a coefficient of friction less than the coefficient of friction of the peripheral outer surface 1222 of the first portion 1214. Thus, the lower coefficient of friction of the second portion 1216 may facilitate insertion of the member 1210 into an ear canal, while the higher coefficient of friction of the first portion 1214 may facilitate retention of the member 1210 in an ear canal.

Foam ear tip ease of insertion and removal testing was done using a Dillon Quantrol Advanced Force Gauge AFG100N attached to a Quantrol motorized test stand. This instrument is available from Quantrol Inc., 1000 Armstrong Drive, Fairmont, Minn. 56031-1439. The test surface used was a 304 stainless steel test plate, TP-25, obtained from Cheminstruments Inc, 510 Commercial Drive, Fairfield Ohio 45014. The stainless steel test panel was mounted on an aluminum base plate which held the test panel at an angle of 10 degrees from vertical. The foam tip was mounted to the Dillon Quantrol force gauge using a threaded screw insert like that used by Hearing Components Comply™ Canal Tip compliant ear mold product.

Foam samples used in this study were cut with a cross sectional area of 0.237 sqin. The length of the samples was 0.63". A hole was die cut in the center of the foam sample and a Comply Canal Tip center insert with a screw thread was glued into the die cut hole. The center insert was made from Huntsman A65P4324 polyurethane.

The initial measurement made on the foam ear tip was to test the insertion force of the foam tip with the skin side of the foam tip oriented towards the stainless steel test panel. The test was initialized by bringing the foam tip into contact with the stainless steel test panel until a force of 0.005 lb registered on the force gauge. The test measurement was started by moving the foam ear tip/force gauge assembly downward at 2 inch/minute for 15 seconds. The peak compression force registered on the force gauge was recorded as the insertion force. The movement of the foam tip was stopped after the 15 second insertion force measurement and was then moved upward at 2 inch/minute. The maximum tensile force measured during this part of the test was recorded as the removal force of the tip. The stainless steel test panel was cleaned with acetone between tests. Results of the insertion/removal force measurements are contained in the attached spread sheet.

The effect of reducing the coefficient of friction on the leading edge of the foam ear tip to provide an easier insertion into the ear canal was simulated by adding a film to cover the skin surface of the foam ear tip which would enter the ear first. The films were applied to the foam using 3M transfer tape #924. The foam did not extend up the side of the foam ear tip in this second sample configuration. A low coefficient of friction film used in these examples was Cotran 9720 polyethylene film available from 3M Company, 3M Center, Building 42-6E-37, St. Paul, Minn. 55144. The Cotran film was applied with the matt finish side oriented out. A second type of low coefficient of friction film used was a microporous polyethylene film available from RKW USA Inc., 3 Central Plaza, 501 Broad St., Suite 325, Rome, Ga. 30161 as Code 749 film. The insertion and removal forces were measured as described above using this second sample configuration.

A further improvement in the insertion of the foam ear tip into the ear canal was tested using a third sample configuration. In this configuration the Cotran polyethylene film/RKW Code 749 film was applied to cover the skin surface of the foam ear tip and the film also extend up the side of the foam ear tip by approximately ¼". The insertion and removal forces were measured as described above.

In addition to using the polyethylene films to lower the insertion force of the foam ear tips, a dry lubricating film forming coating was used to coat the outer surface of the Comply Canal Tip foam. The top inch of the Canal Tip foam samples were coated with a film forming dry lubricant called Emralon 8301-01 supplied by the Acheson Colloids Company, 1600 Washington Avenue, Port Huron, Mich. 48060. This coating was allowed to dry before retesting. After the coating had dried, the insertion and removal forces of the coated Canal Tip foam ear tip were measured as described above.

Foam samples used in these examples are as follows.
1. Comply Canal Tip foam available from Hearing Components, 420 Hayward Ave. N., Oakdale Minn., 55128.
2. Argus earplug foam available from Argus Corporation a Division of Lendell Manufacturing Inc., 5301 S. Graham Road, St. Charles, Mich. 48655.
3. Aearo Classic Soft foam available from Aearo Company, 8001 Woodland Drive, Indianapolis, Ind. 46278.
4. Federal Foam Technologies ear plug material available from Federal Foam Technologies, 600 Wisconsin Drive, New Richmond, Wis. 54017.

The compressional modulus and the recovery time of each of the foam samples were measured for these examples. The modulus measurement was performed using the Dillon Quantrol Advanced Force Gauge AFG 100N attached to a Quantrol motorized test stand. Vertical movement of the force gauge was indicated using a dial indicator accurate to +/−0.001" of displacement. A ¾" diameter compression plate was attached to the Quantrol force gauge for compressing the foam sample against a steel base plate. To make the measurement, the foam sample was allowed to equilibrate to the ambient temperature and humidity present in the testing room (73 deg. F., 29% Relative Humidity). The test was initialized by placing the foam sample on the steel base plate under the compression plate attached to the Quantrol force gauge. The compression plate was lowered until it just came in contact with the top of the foam sample (indicated when the force gauge would register a force of 0.005 lb.). The foam sample was then compressed 30% by moving the compression plate downward at a rate of 12"/minute. The peak force registered by the force gauge was recorded and divided by the cross sectional area of the foam sample to give the compressional modulus in psi.

The measurement of the recovery time for the foam sample was done as a second part of the compression of the foam sample. After compressing the foam sample 30% in the compressional modulus test, the foam was held at 30% compression for 3 minutes. After 3 minutes the compression plate was moved upward at 12"/minute until it reached 80% of the original height dimension of the foam sample. The recovery time was taken as the time in seconds it took the foam sample to recover 80% of its original height dimension.

| Foam Samples | Low COF Film Type Used | Foam Only Insertion Force (lb·f) | Foam Only Removal Force (lb·f) | Film on Foam Face and Side Insertion Force (lb·f) | Film on Foam Face and Side Removal Force (lb·f) | Foam Compressional Modulus (psi) | Foam Recovery Time (sec) |
|---|---|---|---|---|---|---|---|
| Aearo Classic Soft | Cotran 9720 | 0.46 | 0.07 | 0.162 | 0.0367 | 11.5 | 158 |
| Argus | Cotran 9720 | 0.428 | 0.093 | 0.238 | 0.072 | 22.8 | 196 |
| Comply Canal Tip | Emralon 8301 | 0.926 | 0.02 | 0.601 | 0.127 | 8.7 | 50 |
| Federal Foam Tech. | Code 749 | 1.385 | 0.025 | 0.468 | 0.12 | 6.9 | 11 |
| Elastic Nolatex | Cotran 9720 | 0.122 | 0.025 | 0.106 | 0.028 | 1.1 | 0 |
| Swisstex SAF6060 | Code 749 | 0.06 | 0.005 | 0.053 | 0.018 | 0.6 | 7 |

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A user-disposable member for placement within the auditory anatomy of a user, the user-disposable member comprising:
    a polymeric foam body having a central longitudinal axis, the polymeric body including a first portion having a peripheral outer surface located radially outward from the central longitudinal axis, and a second portion having a peripheral outer surface located radially outward from the central longitudinal axis;
    wherein the peripheral outer surface of the first portion has surface characteristics providing a first coefficient of friction between the peripheral outer surface of the first portion and a surface of an ear canal, and the peripheral outer surface of the second portion has surface characteristics providing a second coefficient of friction between the peripheral outer surface of the second portion and the surface of the ear canal, the second coefficient of friction being less than the first coefficient of friction, the surface characteristics of the peripheral outer surface of the first portion being dissimilar from the surface characteristics of the peripheral outer surface of the second portion.

2. The user-disposable member of claim 1, wherein the polymeric foam body comprises a slow recovery polymeric foam.

3. The user-disposable member of claim 1, wherein the polymeric foam body comprises a viscoelastic polymeric foam.

4. The user-disposable member of claim 1, wherein the peripheral outer surface of the first portion comprises a cut outer surface, and the peripheral outer surface of the second portion comprises a molded outer surface.

5. The user-disposable member of claim 1, wherein the peripheral outer surface of the second portion includes a skin layer, and the peripheral outer surface of the first portion is devoid of a skin layer.

6. The user-disposable member of claim 1, wherein the peripheral outer surface of the second portion includes a lubricious polymeric film.

7. The user-disposable member of claim 1, wherein the peripheral outer surface of the first portion has visible cellular interstices, and the peripheral outer surface of the second portion has enclosed cellular interstices.

8. The user-disposable member of claim 1, wherein the peripheral outer surface of the first portion has a first porosity and the peripheral outer surface of the second portion has a second porosity different from the first porosity.

9. The user-disposable member of claim 1, wherein the first portion comprises a first polymeric foam material and the second portion comprises a second polymeric foam material dissimilar from the first polymeric foam material.

10. The user-disposable member of claim 1, wherein the first portion comprises a generally cylindrical shape.

11. The user-disposable member of claim 1, wherein the second portion comprises a frusta-conical shape.

12. The user-disposable member of claim 1, wherein the second portion includes a tapered region and the first portion includes a cylindrical region.

13. The user-disposable member of claim 1, wherein the body includes a lumen extending through at least a portion of the body.

14. The user-disposable member of claim 13, further comprising a polymeric member disposed in the lumen.

15. A user-disposable member for placement within the auditory anatomy of a user, the user-disposable member comprising:
- a polymeric foam body including a first portion and a second portion;
- wherein the first portion has a generally cylindrical shape having a cylindrical outer surface, wherein at least a portion of the cylindrical outer surface has surface characteristics providing a first coefficient of friction between the cylindrical outer surface and a surface of an ear canal;
- wherein the second portion has a generally frusta-conical shape having a frusta-conical outer surface, wherein at least a portion of the frusta-conical outer surface has surface characteristics providing a second coefficient of friction between the frusta-conical outer surface and the surface of the ear canal; and
- wherein the surface characteristics of the cylindrical outer surface are dissimilar from the surface characteristics of the frusta-conical outer surface such that the first coefficient of friction is greater than the second coefficient of friction.

16. The user-disposable member of claim 15, wherein the first portion comprises a first polymeric foam material, and the second portion comprises a second polymeric foam material different from the first polymeric foam material.

17. The user-disposable member of claim 15, wherein the cylindrical outer surface of the first portion has a first porosity and the frusta-conical outer surface of the second portion has a second porosity different from the first porosity.

18. The user-disposable member of claim 15, wherein the frusta-conical outer surface of the second portion includes a lubricious polymeric film.

19. An assembly for transmitting sound to an ear canal of a user, the assembly comprising:
- a sound control device including a connecting portion, the connecting portion having a proximal end, a distal end and a lumen defining a sound tube extending therebetween; and
- a user-disposable member coupled to the connecting portion, the user-disposable member comprising a polymeric foam body having a central longitudinal axis, the polymeric body including a first portion having a peripheral outer surface located radially outward from the central longitudinal axis, and a second portion having a peripheral outer surface located radially outward from the central longitudinal axis;
- wherein the peripheral outer surface of the first portion has surface characteristics providing a first coefficient of friction between the peripheral outer surface of the first portion and a surface of an ear canal, and the peripheral outer surface of the second portion has surface characteristics providing a second coefficient of friction between the peripheral outer surface of the second portion and the surface of the ear canal, the second coefficient of friction being less than the first coefficient of friction, the surface characteristics of the peripheral outer surface of the first portion being dissimilar from the surface characteristics of the peripheral outer surface of the second portion.

20. The assembly of claim 19, wherein the connecting portion includes a means for coupling the user-disposable member to the connecting portion.

21. The assembly of claim 19, wherein the peripheral outer surface of the first portion is a cut outer surface and the peripheral outer surface of the second portion is a molded outer surface.

22. The assembly of claim 19, wherein the peripheral outer surface of the first portion has a first porosity and the peripheral outer surface of the second portion has a second porosity different from the first porosity.

23. The assembly of claim 19, wherein the first portion comprises a first polymeric foam material and the second portion comprises a second polymeric foam material dissimilar from the first polymeric foam material.

24. The assembly of claim 19, wherein the peripheral outer surface of the second portion includes a skin layer, and the peripheral outer surface of the first portion is devoid of a skin layer.

* * * * *

UNITED STATES PATENT AND TRADEMARK OFFICE
CERTIFICATE OF CORRECTION

PATENT NO.      : 7,600,604 B2  Page 1 of 1
APPLICATION NO. : 11/347600
DATED           : October 13, 2009
INVENTOR(S)     : Babcock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 667 days.

Signed and Sealed this

Fifth Day of October, 2010

David J. Kappos
*Director of the United States Patent and Trademark Office*